US012710388B2

(12) United States Patent
Turner et al.

(10) Patent No.: US 12,710,388 B2
(45) Date of Patent: Aug. 18, 2026

(54) SMOOTH AND BIODEGRADABLE NANO-CELLULOSE COMPOSITES FOR PRINTED ELECTRONICS

(71) Applicant: The Trustees of the University of Pennsylvania, Philadelphia, PA (US)

(72) Inventors: Kevin T. Turner, Wayne, PA (US); Gokulanand Meenakshisundaram Iyer, Astoria, NY (US); Gnana Saurya Vankayalapati, St. Paul, MN (US); Michael David Machold, Philadelphia, PA (US); Roy Harold Olsson, III, Phoenixville, PA (US); Anne-Marie Zaccarin, Montréal (CA)

(73) Assignee: The Trustees of the University of Pennsylvania, Philadelphia, PA (US)

(*) Notice: Subject to any disclaimer, the term of this patent is extended or adjusted under 35 U.S.C. 154(b) by 175 days.

(21) Appl. No.: 18/640,633

(22) Filed: Apr. 19, 2024

(65) Prior Publication Data

US 2024/0353364 A1 Oct. 24, 2024

Related U.S. Application Data

(60) Provisional application No. 63/497,290, filed on Apr. 20, 2023.

(51) Int. Cl.
*G01N 27/22* (2006.01)
*G01N 33/24* (2006.01)

(52) U.S. Cl.
CPC ......... *G01N 27/223* (2013.01); *G01N 33/246* (2013.01)

(58) Field of Classification Search
CPC ........ G01N 27/00; G01N 27/02; G01N 27/22; G01N 33/00; G01N 33/24; G01N 27/223; G01N 33/246
USPC ......................... 324/600, 649, 658, 686, 689
See application file for complete search history.

(56) References Cited

U.S. PATENT DOCUMENTS

| | | | | |
|---|---|---|---|---|
| 9,448,195 | B2 * | 9/2016 | Moreno | C12M 41/46 |
| 10,766,004 | B2 * | 9/2020 | Zhou | B01D 61/366 |
| 10,981,122 | B2 * | 4/2021 | Hoshino | B01D 71/4011 |

(Continued)

FOREIGN PATENT DOCUMENTS

| | | | | |
|---|---|---|---|---|
| CN | 104114479 A | * | 10/2014 | B01D 67/00793 |
| CN | 106486678 A | * | 3/2017 | H01M 12/08 |
| WO | WO-2015103063 A1 | * | 7/2015 | B01D 61/366 |

(Continued)

OTHER PUBLICATIONS

Meng et al., "Mechanics of strong and tough cellulose nanopaper," applied mechanics reviews, vol. 71, Issue 4, Jul. 2019, pp. 30.

(Continued)

*Primary Examiner* — Hoai-An D. Nguyen
(74) *Attorney, Agent, or Firm* — BakerHostetler

(57) ABSTRACT

A composite, comprising: a first surface, a second surface, and a thickness between the first surface and the second surface, a porous scaffold having a plurality of pores extending from the first surface into the thickness, at least some of the plurality of pores being at least partially filled with cellulose nanofibrils, and the first surface of the composite having a root mean square (RMS) roughness of from about 0.01 to about 0.1 μm.

20 Claims, 26 Drawing Sheets

(56) References Cited

U.S. PATENT DOCUMENTS

2012/0003454 A1* 1/2012 Younes ................ B29C 70/086 264/259

FOREIGN PATENT DOCUMENTS

| | | | |
|---|---|---|---|
| WO | WO-2019188904 A1 * | 10/2019 | ............ G01N 27/12 |
| WO | WO-2022226265 A1 * | 10/2022 | ................ F26B 5/14 |
| WO | WO-2023047061 A1 * | 3/2023 | ............ G09B 23/30 |

OTHER PUBLICATIONS

Mokhena et al., "Thermoplastic processing of PLA/cellulose nanomaterials composites," Polymers, vol. 10, Issue 12, Dec. 2018, pp. 29.
Morais et al., "Influence of paper surface characteristics on fully inkjet printed PEDOT:PSS-based electrochemical transistors", Semiconductor Science and Technology., 2021, vol. 36, 125005.
Moropoulou et al., "The immediate impact of aqueous treatments on the strength of paper," Restaurator, vol. 24, Issue 3, Jan. 2003, pp. 20.
Nakagaito et al., "Novel high-strength biocomposites based on microfibrillated cellulose having nano-order-unit web-like network structure," Applied physics, vol. 80, Issue 1, Jan. 2005, pp. 155-159.
Nissan, "H-bond dissociation in hydrogen bond dominated solids," Macromolecules, vol. 9, Issue 5, Sep. 1976, pp. 840-850.
Okubayashi et al., "Moisture soprtion/desorption behavior of various manmade cellulosic fibers", Journal of Applied Polymer Science, 2005, vol. 97, pp. 1621-1625.
Okubayashi et al., "Water accessibilities of man-made cellulosic Fibers—Effects of fiber characteristics", Cellulose, 2005, vol. 12, pp. 403-410.
Orelma et al., "Surface functionalized nanofibrillar cellulose (NFC) film as a platform for immunoassays and diagnostics," Biointerphases, vol. 7, Issue 1, Dec. 2012, pp. 12.
Orue et al., "Bionanocomposites based on thermoplastic starch and cellulose nanofibers," Journal of Thermoplastic Composite Materials, vol. 29, Issue 6, Jun. 2016, pp. 817-832.
Pai et al., "Mechanical properties of individual electrospun PA 6 (3) T fibers and their variation with fiber diameter," Polymer, vol. 52, Issue 10, May 2011, pp. 2295-2301.
Panaitescu et al., "Polymer composites with cellulose microfibrils," Polymer Engineering & Science, vol. 47, Issue 8, 2007, pp. 1228-1234.
Patra et al., "Effect of solvents on the dynamic viscoelastic behavior of poly (methyl methacrylate) film prepared by solvent casting," Journal of materials science, vol. 46, Issue 15, Aug. 2011, pp. 5044-5049.
Picu., "Mechanics of random fiber networks—a review," Soft Matter, vol. 7, Issue 15, Jul. 2011, pp. 6768-6785.
Placet et al., "Influence of environmental relative humidity on the tensile and rotational behaviour of hemp fibres," Journal of Materials Science, vol. 47, Issue 7, Apr. 2012, pp. 3435-3446.
Qiang et al., "The interplay of polymer bridging and entanglement in toughening polymer-infiltrated nanoparticle films," ACS nano, vol. 16, Apr. 2022, pp. 6372-6381.
Quintana-Alonso. I. et al., "Fracture of brittle lattice materials: A review," Major accomplishments in composite materials and sandwich structures, 2009, pp. 21.
Rajinipriya et al., "Importance of agricultural and industrial waste in the field of nanocellulose and recent industrial developments of wood based nanocellulose: A Review", ACS Sustainable chemistry & Engineering, 2018, vol. 6, pp. 2807-2828.
Reiner et al., "Process scale-up of cellulose nanocrystal production to 25 kg per batch at the forest products laboratory," In: Production and applications of Cellulose, Chapter 1.1, 2013, pp. 21-24.
Reishofer et al., "Humidity response to cellulose thin films", Biomacromolecules, 2022, vol. 23, pp. 1148-1157.
Reuss, Berechnung der Fliebrrenze von Mischkristallen auf grund der plastizitatsbedin-gung fur einkristalle, ZAMM—Zeitschrift fur angewandte mathematik und mechanik, vol. 9, No. 1, pp. 49-58, 1929—Not English.
Ritchie, "The conflicts between strength and toughness," Nature materials, vol. 10, Issue 11, Nov. 2011, pp. 817-822.
Rivadeneyra et al., "Cellulose nanofibers as substrate for flexible and biodegradable moisture sensors", Composites science and technology, 2021, vol. 208, 108738.
River et al., "Contoured wood double cantilever beam specimen for adhesive joint fracture tests," Journal of testing, 1993, p. 8.
Romijn et al., "The fracture toughness of planar lattices: Imperfection sensitivity," Journal of the Mechanics and Physics of Solids, vol. 55, Issue 12, Dec. 2007, pp. 2538-2564.
Ryu et al., "Microstructure, thermal and mechanical properties of composite films based on carboxymethylated nanocellulose and polyacrylamide," Carbohydrate polymers, vol. 211, May 2019, pp. 84-90.
Sain et al., "Improved mechanical and moisture resistance property of in situ polymerized transparent PMMA/Cellulose composites," Polymer Composites, vol. 39, Issue 9, 2015, pp. 1748-1758.
Sain et al., "Synthesis and characterization of PMMA-cellulose nanocomposites by in situ polymerization technique," Journal of applied polymer science, vol. 126, Issue S1, 2012, pp. E127-E134.
Salem et al., "A systematic examination of the dynamics of water-cellulose interactions on capillary force-induced fiber collapse", Carbohydrate Polymers, 2022, vol. 295, 119856.
Santmarti et al., "Transparent poly (methyl methacrylate) composites based on bacterial cellulose nanofiber networks with improved fracture resistance and impact strength," Acs Omega, vol. 4, 2019, pp. 9896-9903.
Sehaqui et al., "Cellulose nanofiber orientation in nanopaper and nanocomposites by cold drawing," ACS Appl. Mater. Interfaces, vol. 4, Issue 2, 2012, pp. 1043-1049.
Seydibeyoglu et al., "Novel nanocomposites based on polyurethane and micro fibrillated cellulose," Composites science and technology, vol. 68, Issue 3, Mar. 2008, pp. 908-914.
Shaker et al., "Inkjet printing of ultrawideband (UWB) Antennas on Paper-Based substrates", IEEE Antennas and Wireless propagation Letters, 2011, vol. 10, pp. 111-114.
Shi et al., "Carboxylated nanocellulose/poly (ethylene oxide) composite films as solid-solid phase-change materials for thermal energy storage," Carbohydrate polymers, vol. 225, Dec. 2019.
Shih et al., "Highly transparent and impact-resistant PMMA nanocomposites reinforced by cellulose nanofibers of pineapple leaves modified by eco-friendly methods," Express Polymer letters, vol. 12, Issue 9, 2018, pp. 844-854.
Shivyari et al., "Production and characterization of laminates of paper and cellulose nanofibrils," ACS applied materials & interfaces, vol. 8, Issue 38, Sep. 2016, pp. 25520-25528.
Solhi et al., "Understanding nanocellulose-water interactions: turning a detriment into an asset", Chemical reviews, 2023, vol. 123, pp. 1925-2015.
Spiewak et al., "Humidity dependence of fracture toughness of cellulose fibrous networks," Engineering fracture mechanics, vol. 264, Apr. 2022, p. 24.
Srawley et al., "Stress intensity factors for bend and compact specimens," Engineering Fracture Mechanics, vol. 4, Issue 3, 1972, pp. 587-589.
Steigerwald et al., "Plane strain fracture toughness of high strength materials," Engineering Fracture Mechanics, 1969, vol. 1, pp. 473-494.
Syrovy et al., "Wide range humidity sensors printed on biocomposite films of cellulose nanofibril and poly(ethylene glycol)", Journal of Applied Polymer Science, 2019, vol. 136, 47920.
Tanaka et al., "Deformation and fracture of paper during the in-plane fracture toughness testing—Examination of the essential work of racture method," Journal of materials science, 2000, pp. 7.
Tankasala et al., "2013 Koiter medal paper: crack-tip fields and toughness of two-dimensional elastoplastic lattices," Journal of applied mechanics, vol. 82, Issue 9, Sep. 2015, pp. 31.

(56) References Cited

OTHER PUBLICATIONS

Tibolla et al., "Banana starch nanocomposite with cellulose nanofibers isolated from banana peel by enzymatic treatment: In vitro cytotoxicity assessment," Carbohydrate Polymers, vol. 207, Mar. 1, 2019, pp. 169-179.
Tomczynska-Mleko et al., "New product development: Cellulose/egg white protein blend fibers," Carbohydrate polymers, vol. 126, Aug. 2015, pp. 168-174.
Tong et al., "Flexible Hybrid Electronics: Review and Challenges", 2018 IEEE International Symposium on Circuits and Systems (ISCAS), Florence, 2018, pp. 1-5.
Toribio et al., "A critical review of stress intensity factor solutions for surface cracks in round bars subjected to tension loading," Engineering failure analysis, vol. 16, Issue 3, Apr. 2009, pp. 794-809.
Torstensen et al., "Swelling and free-vol. characteristics of TEMPO-Oxidized Cellulose nanofibril films", Biomacromolecules, 2018, vol. 19, pp. 1016-1025.
Torvinen et al., "Smooth and Flexible filler-nanocellulose composite structure for printed electronics applications", Cellulose, 2012, vol. 19, pp. 821-829.
Turek, "On the tensile testing of high modulus polymers and the compliance correction," Polymer Engineering & Science, vol. 33, Issue 6, 1993, pp. 328-333.
Vallittu, "High-aspect ratio fillers: fiber-reinforced composites and their anisotropic properties," Dental materials, vol. 31, Issue 1, Jan. 2015, pp. 7.
Vankayalapati et al., "Toughening poly (methyl methacrylate) via reinforcement with cellulose nanofibrils," ACS Applied Polymer Materials, vol. 3, Issue 12, Dec. 2021, pp. 6102-6110.
Venugopal et al., "Reinforcement of natural rubber using cellulose nanofibres isolated from Coconut spathe," Materials Today, vol. 5, Issue 8, 2018, pp. 16724-16731.
Vitale, "Effects of water on the mechanical properties of paper and their relationship to the treatment of paper," MRS Proceedings, vol. 267, 1992.
Wang et al. "Flexible Electronics and Healthcare Applications", Frontiers in Nanotechnology, 2021, vol. 3, 625989.
Wang et al., "Flexible RFID tag metal antenna on Paper-based substrate by Inkjet printing technology", Advanced functional materials., 2019, vol. 29, 1902579.
Wang et al., "Flexible Sensing Electronics for Wearable/Attachable ealth Monitoring", Small, 2017, vol. 13, 1602790.
Wang et al., "Preparation of nanocellulose/filter paper (NC/FP) composite membranes for high-performance filtration," Cellulose, vol. 26, Issue 2, Jan. 2019, pp. 1183-1194.
Wanigaratne et al., "Comparison of fracture toughness of paper with tensile properties," Appita journal, Sep. 2002, pp. 369-385.
Watson et al., "Mode I traction-separation measured using rigid double cantilever beam applied to structural adhesive," The Journal of adhesion, Aug. 2018, pp. 21.
Wei et al., "Effect of patterned inclusions on the fracture behavior of ceramic composites," Composites Part B: Engineering, vol. 172, Sep. 2019, pp. 564-592.
Wiederhorn et al., "Critical analysis of the theory of the double cantilever method of measuring fracture-surface energies," Journal of applied physics, vol. 39, Issue 3, Feb. 1968. pp. 1569-1572.
Wu et al., "Ultrastrong and high gas-barrier nanocellulose/clay-layered composites," Biomacromolecules, vol. 13, Issue 6, Jun. 2012, pp. 1927-1932.
Xie et al., "The water vapour sorption behaviour of three celluloses: analysis using parallel exponential kinetics and interpretation using Kelvin-Voight viscoelastic model", Cellulose, 2011, vol. 18, pp. 517-530.
Yahyazadehfar et al., "On the mechanics of fatigue and fracture in teeth," Applied mechanics reviews, vol. 66, Issue 3, May 2014, pp. 19.
Yang et al., "RFID tag and RF structures on a paper substrate using inkjet-printing technology", IEEE transactions on microware theory and techniques, 2007, vol. 55, pp. 2894-2901.
Zaccarin et al., "Fabrication and Characterization of soil moisture sensors on a biodegradable, cellulose-based substrate", IEEE Sensors Journal, 2023.
Zauscher et al., "The influence of water on the elastic modulus of paper," Tappi journal, 1996, pp. 5.
Zechner et al., "Paper multilayer with a fracture toughness of steel," Journal of Materials Science, vol. 48, Issue 15, Aug. 2013, pp. 5180-5187.
Zhang et al., "Reinforcing natural rubber with cellulose nanofibrils extracted from bleached eucalyptus kraft pulp," Journal of Biobased Materials and Bioenergy, vol. 8, Issue 3, Jun. 2014, pp. 317-324.
Zhao et al., "Orientation and relaxation in uniaxially stretched poly (methyl methacrylate)-poly (ethylene oxide) blends," Polymer, vol. 30, Issue 9, Sep. 1989, pp. 1643-1650.
Zhao et al., "The fracture resistance of bi-axially orientated PMMA," IOP Conference Series: Materials Science and Engineering, vol. 770, 2020, pp. 9.
Zhao et al., "Using cellulose nanofibers to reinforce polysaccharide films: Blending vs layer-by-layer casting," Carbohydrate polymers, vol. 227, Jan. 2020.
Zheng et al., "Green synthesis of polyvinyl alcohol (PVA)-cellulose nanofibril (CNF) hybrid aerogels and their use as superabsorbents," Journal of materials Chemistry A, vol. 2, Issue 9, Feb. 2014, pp. 3110-3118.
Zheng et al., "Polyvinyl alcohol (PVA)-cellulose nanofibril (CNF)-multiwalled carbon nanotube (MWCNT) hybrid organic aerogels with superior mechanical properties," RSC Advances, vol. 3, Issue 43, Oct. 2013, pp. 20816-20823.
Heide-Jorgensen et al., "Mechanics and fracture of structured pillar interfaces," Journal of the mechanics and physics of solid, 2020, vol. 137, 20 pages.
Heng et al., "Flexible Electronics and Devices as Human-Machine Interfaces for Medical Robotics", Advanced Materials, 2022, vol. 34, 2107902.
Hill et al., "Rheological description of the water vapour sorption kinetics behaviour of wood invoking a model using a canonical assembly of Kelvin-voigt elements and a possible link with sorption hysteresis", Holzforschung, 2012, vol. 66, pp. 35-47.
Hill, "The elastic behaviour of a crystalline aggregate," Proceedings of the Physical Society, vol. 65, Issue 5, 1952.
Hoagland et al., "On the use of the double cantilever beam specimen for determining the plane strain fracture toughness of metals," Journal of basic engineering, vol. 89, Issue 3, 1967, pp. 525-532.
Hossain, "Effective toughness of heterogeneous media," Journal of the Mechanics and Physics of Solids, vol. 71, 2014, pp. 15-32.
Huajian, "Fracture analysis of nonhomogeneous materials via a moduli-perturbation approach," Int. J. Solid, Structures, vol. 27, No. 13. 1991, pp. 1663-1682.
Hubbe et al., "Nanocellulose in thin films, coatings, and plies for packaging applications: A review," Bioresources, vol. 12, Issue 1, Feb. 2017, pp. 2143-2233.
Ihalainen et al., "Influence of surface properties of coated papers on printed Electronics", industrial & Engineering Chemistry Research., 2012, vol. 51, pp. 6025-6036.
Irwin et al., "Analysis of stresses and strains near the end of a crack traversing a plate," Journal of applied mechanics, vol. 24, Issue 3, 1957, pp. 361-364.
Isogai et al., "TEMPO-oxidized cellulose nanofibers", Nanoscale, 2011, vol. 3, pp. 71-85.
Isogai, "Wood nanocelluloses: fundamentals and applications as new bio-based nanomaterials," Journal of wood science, vol. 59, Issue 6, Dec. 2013, pp. 449-459.
Iwamoto et al., "Optically transparent composites reinforced with plant fiber-based nanofibers," Applied physics, vol. 81, Issue 6, Nov. 2005, pp. 1109-1112.
Iwamoto et al., "Relationship between aspect ratio and suspension viscosity of wood cellulose nanofibers," Polymer Journal, vol. 46, Issue 1, Jan. 2014, pp. 73-76.
Jaiswal et al., "Biodegradable cellulose nanocomposite substrate for recyclable flexible printed electronics", Advanced Electronic Materials, 2023, 2201094.

(56) References Cited

OTHER PUBLICATIONS

Jajcinovic et al., "Influence of relative humidity on the strength of hardwood and softwood pulp fibres and fibre to fibre joints," Cellulose, vol. 25, Issue 4, Apr. 2018, pp. 2681-2690.
Johansson et al., "Renewable fibers and bio-based materials for packaging applications—a review of recent developments," BioResources, 2012, pp. 47.
Jorgensen et al., "Crack growth along heterogeneous interface during the DCB experiment," International Journal of Solids and Structures, vol. 120, Aug. 1, 2017, pp. 278-291.
Kajanto et al., "The potential use of micro-and nanofibrillated cellulose as a reinforcing element in paper," Journal of science & technology for forest product and process, vol. 2, Issue 7, 2012, pp. 42-48.
Kannien, "An augmented double cantilever beam model for studying crack propagation and arrest," International Journal of fracture, vol. 9, Issue 1, 1973, pp. 83-92.
Kant et al., "Fracture behavior of individual carbon fibers in tension using nano-fabricated notches," Composites science and technology, vol. 89, Dec. 2013, pp. 83-88.
Kasmani et al., "Effect of nano-cellulose on the improvement of the properties of paper newspaper produced from chemi-mechanical pulping," BioResources, 2019, pp. 15.
Kedzior et al., "Poly (methyl methacrylate)-grafted cellulose nanocrystals: One-step synthesis, nanocomposite preparation, and characterization," The Canadian Journal of Chemical Engineering, vol. 94, Issue 5, 2016, pp. 811-822.
Kerry et al., "Smart packaging technologies for fast moving consumer goods," John Wiley & Sons, 2008.
Khan et al., "A.C.A. New Frontier of Printed Electronics: Flexible Hybrid Electronics", Advanced Materials., 2020, vol. 32, 1905279.
Kim et al., "An RFIDenabled inject-printed soil moisture sensor on paper for “smart” Agricultural applications", IEEE Sensors 2014 Proceedings, Valencia, Spain, 2014, pp. 1507-1510.
Kim et al., "Fatigue crack propagation in poly (methyl methacrylate): effect of molecular weight and internal plasticization," Polymer Engineering & Science, 1977.
Kim et al., "Inkjet-printed antennas, sensors and circuits on paper substrate", IET Microwaves, Antennas & Propagation, 2013, vol. 7, pp. 858-868.
Kiziltas et al., "Cellulose NANOFIBER-polyethylene nanocomposites modified by polyvinyl alcohol," Journal of Applied Polymer Science, vol. 133, Issue 6, 2016, pp. 8.
Kiziltas et al., "Preparation and characterization of transparent PMMA-cellulose-based nanocomposites," Carbon-hydrate polymers, vol. 127, 2015, pp. 381-389.
Kolakovic et al., "Spray-dried cellulose nanofibers as novel tablet excipient," Aaps Pharmscitech, vol. 12, Issue 4, Dec. 2011, pp. 1363-1373.
Korhonen et al., "Hydrophobic nanocellulose aerogels as floating, sustainable, reusable, and recyclable oil absorbents," ACS applied materials & interfaces, vol. 3, Issue 6, Jun. 2011, pp. 1813-1816.
Larsson et al., Compression of Coating Structures During Calendering, 2006.
Latifah et al., "Extraction of nanofibrillated cellulose from Kelempayan (*Neolamarckia cadamba*) and its use as strength additive in papermaking," Journal of Tropical Forest Science, vol. 32, Issue 2, 2020, pp. 170-178.
Le Bras et al., "Characterization of Dielectric Properties of Nanocellulose from Wood and Algae for Electrical Insulator Applications", The Journal of physical chemistry B., 2015, vol. 119, pp. 5911-5917.
Lee et al., "Bending and buckling of wet paper," Physics of Fluids, vol. 28, Issue 4, Apr. 2016, pp. 12.
Leng et al., "Thermal insulating and mechanical properties of cellulose nanofibrils modified polyurethane foam composite as structural insulated material," Forest, vol. 10, Issue 2, Feb. 2019, pp. 12.
Li et al., "A paper-based screen printed HF RFID reader antenna system", IEEE journal of radio frequency identification, 2018, pp. 118-126.
Linvill et al., "The combined effects of moisture and temperature on the mechanical response of paper," Experimental mechanics, vol. 54, Issue 8, Oct. 2014, pp. 1329-1341.
Littunen et al., "Network formation of nanofibrillated cellulose in solution blended poly (methyl methacrylate) composites," Carbohydrate polymers, vol. 91, Issue 1, Jan. 2013, pp. 183-190.
Liu et al., "Fabrication and properties of transparent polymethylmethacrylate/cellulose nanocrystals composites," Bioresource technology, vol. 101, Issue 14, Jul. 2010, pp. 5685-5692.
Liu et al., "Mechanical performance of cellulose nanofibril film-wood flake laminate," Holzforschung, vol. 68, Issue 3, Apr. 2014, pp. 283-290.
Liu et al., "The effective Young's modulus of composites beyond the Voigt estimation due to the Poisson effect," Composites Science and Technology, vol. 69, Issue 13, Oct. 2009, pp. 2198-2204.
Long et al., "Fracture toughness of hydrogels: measurement and interpretation," Soft Matter, vol. 12, Issue 39, 2016, pp. 8069-8086.
Lundahl et al., "Strength and Water Interactions of Cellulose I Filaments Wet-Spun from Cellulose nanofibril Hydrogels", Scientific Reports, 2016, vol. 6, 30695.
Luo et al., "A mini-review on the dielectric properties of cellulose and nanocellulose-based materials as electronic components", Carbohydrate Polymers, 2023, vol. 303, 120449.
Macdonald et al., "Latest advances in substrates for flexible electronics", Journal of the society for information display, 2007, vol. 15, 1075.
Mai et al., "In-plane fracture toughness measurement of paper," Fracture Mechanics, 1995, pp. 13.
Mariani et al., "Printing and mechanical characterization of cellulose nanofibril materials", Cellulose, 2019, vol. 26, pp. 2639-2651.
Martinez et al., "Essential work of fracture, crack tip opening displacement, and J-integral relationship for a ductile polymer film," Polymer Testing, vol. 55, Oct. 2016, pp. 247-256.
Andres Valiente Cancho, Criterios de fractura para alambres, Ph.d, E.T.S.I Caminos, Canales y Puertos (UPM), Sep. 1980—Not English.
ASTM D5528-13. Test method for mode I Interlaminar fracture toughness of unidierctional fiber-reinforced polymer matrix composites. technical report, ASTM International, 2013.
Atkins et al., "Time-temperature dependent fracture toughness of Pmma," Journal of Materials Science, vol. 10, Issue 8, 1975, pp. 1381-1393.
Ayissi et al., "Environmentally-friendly cellulose nanofibre sheets for humidity sensing in microwave frequencies", Sensors and Actuators B: Chemical, 2017, vol. 245, pp. 484-492.
Banerjee et al., "Surface treatment of cellulose fibers with methylmethacrylate for enhanced properties of in situ polymerized PMMA/cellulose composites," Journal of Applied Polymer Science, vol. 131, Issue 2, 2014.
Barron et al., "Enhancement of Modulus, Strength, and Toughness in Poly(methyl methacrylate)-Based Composites by the Incorporation of Poly(methyl methacrylate)-Functionalized Nanotubes," materials, vol. 16, Issue 12, 2006, pp. 1608-1614.
Benbow et al., "Experiments on Controlled Fractures," Proceedings of the Physical Society. Section B, vol. 70, Issue 2, 1957, pp. 201-211.
Benitez et al., "Humidity and Multiscale Structure Govern Mechanical Properties and Deformation Modes in Films of Native Cellulose Nanofibrils," Biomacromolecules, vol. 14, Issue 12, 2013, pp. 4497-4506.
Benzeggagh et al., "Measurement of mixed-mode delamination fracture toughness of unidirectional glass/epoxy composites with mixed-mode bending apparatus," Composites Science and Technology, vol. 56, Issue 4, 1996, pp. 439-449.
Bhattacharya et al., "Nanofibrillar cellulose hydrogel promotes three-dimensional liver cell culture," Journal of Controlled Release, vol. 164, Issue 3, Dec. 28, 2012, pp. 291-298.
Bhattacharya, "Polymer nanocomposites—a comparison between carbon nanotubes, graphene, and clay as nanofillers," Materials, vol. 9, Issue 4, 2016, pp. 35.

(56) References Cited

OTHER PUBLICATIONS

Bower et al., "A three-dimensional analysis of crack trapping and bridging by tough particles," Journal of the Mechanics and Physics of Solids, vol. 39, Issue 6, 1991, pp. 815-858.
Brach et al., "Anisotropy of the effective toughness of layered media," Journal of the Mechanics and Physics of Solids, vol. 131, 2019, pp. 96-111.
Bulota et al., "Acetylated microfibrillated cellulose as a toughening agent in poly (lactic acid)," Journal of Applied Polymer Science, vol. 126, 2012, pp. E449-E458.
Carpinteri, "Stress intensity factors for straight-fronted edge cracks in round bars," Engineering Fracture Mechanics, vol. 42, Issue 6, Aug. 1992, pp. 1035-1040.
Caulfield, "Effect of moisture and temperature on the mechanical properties of paper," Materials science, 1997, p. 13.
Celino et al., "The hygroscopic behavior of plant fibers: a review," Front. Chem., vol. 1, 2014, pp. 12.
Cheng et al., "Effects of process and source on elastic modulus of single cellulose fibrils evaluated by atomic force microscopy," Composites Part A: Applied Science and Manufacturing, vol. 40, Issue 5, May 2009, pp. 583-588.
Clarkson et al, "Melt spinning of cellulose nanofibril/polylactic acid (CNF/PLA) composite fibers for high stiffness," ACS Appl. Polym. Mater., vol. 1, Issue 2, 2019, pp. 160-168.
Croon et al., "Line edge roughness: characterization, modeling and impact on device behavior", Digest. International electron devices meeting., San Francisco, 2002, pp. 307-310.
Dastjerdi et al., "Direct measurement of the cohesive law of adhesives using a rigid double cantilever beam technique," Experimental mechanics, vol. 53, Issue 9, Nov. 2013, pp. 1763-1772.
Deo et al., "Effect of moisture absorption on Mechanical properties of Chopped Natural Fiber Reinforced Epoxy Composite", Journal of Reinforced Plastics and Composites, 2010, vol. 29, pp. 2513-2521.
Diez et al., "Functionalization of nanofibrillated cellulose with silver nanoclusters: fluorescence and antibacterial activity," Macromol. Biosci., vol. 11, 2011, pp. 1185-1191.
Dillard et al., "A review of Winkler's foundation and its profound influence on adhesion and soft matter applications," Soft matter, vol. 14, Issue 19, 2018, pp. 3669-3683.
Dong et al., "Cellulose nanocrystals as a reinforcing material for electrospun poly (methyl methacrylate) fibers: Formation, properties and nanomechanical characterization," Carbohydrate Polymers, vol. 87, 2012, pp. 2488-2495.
Dong et al., "Highly transparent and toughened poly (methyl methacrylate) nanocomposite films containing networks of cellulose nanofibrils," ACS Appl. Mater. Interfaces, vol. 7, Issue 45, 2015, pp. 25464-25472.
Evans et al., "Toughening of ceramics by circumferential microcracking," Journal of the American Ceramic Society, vol. 64, Issue 7, 1981, pp. 384-398.
Faber et al., "Crack deflection processes—I. Theory," Acta metallurgica, vol. 31, Issue 4, Apr. 1983, pp. 565-576.
Fahma et al., "The morphology and properties of poly (methyl methacrylate)-cellulose nanocomposites prepared by immersion precipitation method," Journal of applied polymer science, vol. 128, Issue 3, 2013, pp. 1563-1568.
Fukuzumi et al., "Transparent and high gas barrier films of cellulose nanofibers prepared by TEMPO-mediated oxidation," Biomacromolecules, vol. 10, Issue 1, 2009, pp. 162-165.
Gamstedt, "Moisture induced softening and swelling of natural cellulose fibres in composite applications," IOP conference series: materials science and engineering, 2016, pp. 13.
Gao et al., "A first-order perturbation analysis of crack trapping by arrays of obstacles," Journal of applied mechanics, vol. 56, Issue 4, 1989, pp. 828-836.
Garcia et al., "The future of plastics recycling", Science, 2017, vol. 358, pp. 870-872.
Gehlen et al., "Kinetics of autocatalytic acid hydrolysis of cellulose with crystalline and amorphouse fractions", Cellulose, 2010, vol. 17, pp. 245-252.
Gillis et al., "Double-cantilever cleavage mode of crack propagation," Journal of applied physics, vol. 35, Issue 3, 1964, pp. 647-658.
Gilman et al., "Direct measurements of the surface energies of crystals," Journal of applied physics, vol. 31, Issue 12, 1960, pp. 2208-2218.
Gojny et al., "Carbon nanotube-reinforced epoxy-composites: enhanced stiffness and fracture toughness at low nanotube content," Composites science and technology, vol. 64, Issue 15, 2004, pp. 2363-2371.
Gonzalez et al., "Nanofibrillated cellulose as paper additive in eucalyptus pulps," Bioresources, vol. 7, Issue 4, Sep. 2012, pp. 5167-5180.
Gotham et al., "Effect of molecular orientation on the fracture toughness of thermoplastics," Polymer, vol. 19, Issue 3, Mar. 1978, pp. 341-347.
Gowrishankar et al., "A comparison of direct and iterative methods for determining traction-separation relations," International journal of fracture, vol. 177, Issue 2, Oct. 2012, pp. 109-128.
Griffith et al., "VI. The phenomena of rupture and flow in solids," Philosophical transactions of the royal society of london, vol. 221, Jan. 1921, pp. 163-198.
Gross et al., "Plane elastostatic analysis of V-notched plates," International journal of fracture mechanics, vol. 8, Issue 3, Sep. 1972, pp. 267-276.
Gross et al., "Stress-intensity factors for a single-edge-notch tension specimen by boundary collocation of a stress function," National aero nautics and space administration, 1994, pp. 16.
Gu et al., "Experimental study of modulus, strength and toughness of 2D triangular lattices," International Journal of Solids and Structures, vol. 152-153, Nov. 2018, pp. 207-216.
Gunderson, "The compressive load-strain curve of paperboard: rate of load and humidity effects," Journal of pulp and paper science, 1988, pp. 7.
Guo et al., "Water vapor sorption properties of cellulose nanocrystals and nanofibers using dynamic vapor sorption apparatus", Scientific Reports, 2017, vol. 7, 14207.
Hasan et al., "Tuning physical, mechanical and barrier properties of cellulose nanofibril films through film drying techniques coupled with thermal compression", Cellulose, 2021, vol. 28, pp. 11345-11366.
Hashin, "Analysis of composite materials—a survey," Journal of applied mechanics, vol. 50, Issue 3, 1983, pp. 481-505.
Haslach, "The moisture and rate-dependent mechanical properties of paper: a review," Mechanics of time-dependent materials, vol. 4, Issue 3, 2000, pp. 169-210.
Baez et al, "Influence of drying restraint on physical and mechanical properties of nanofibrillated cellulose films," Cellulose, 2014, vol. 21, Issue 1, pp. 347-356.

* cited by examiner

Press solution to form thin, continuous layer

Cardstock
Acrylic

Deposit CNF solution

Cardstock
Acrylic

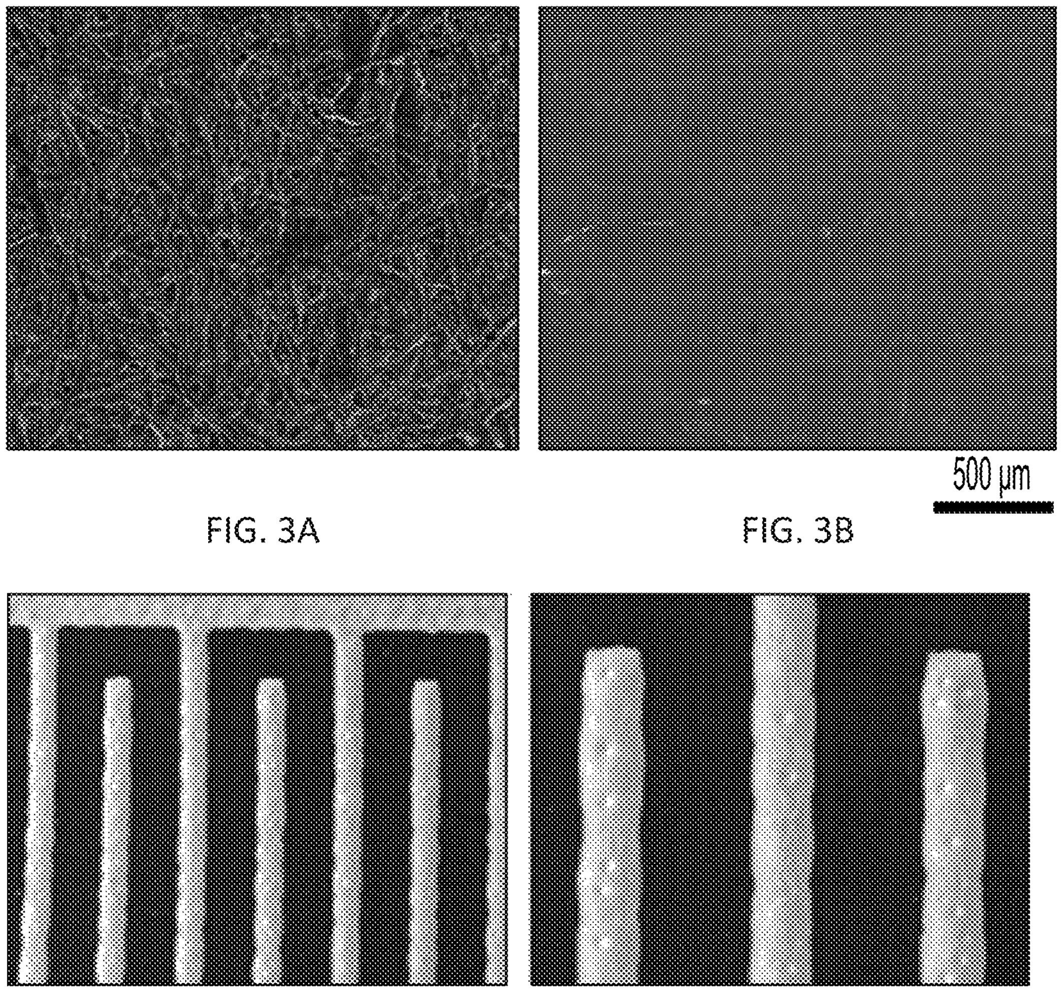
FIG. 3A
FIG. 3B
FIG. 3C
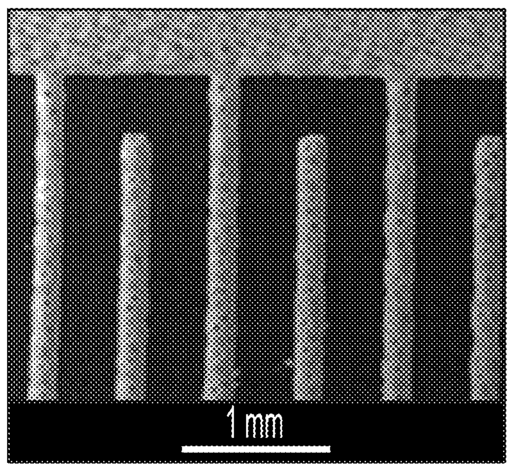
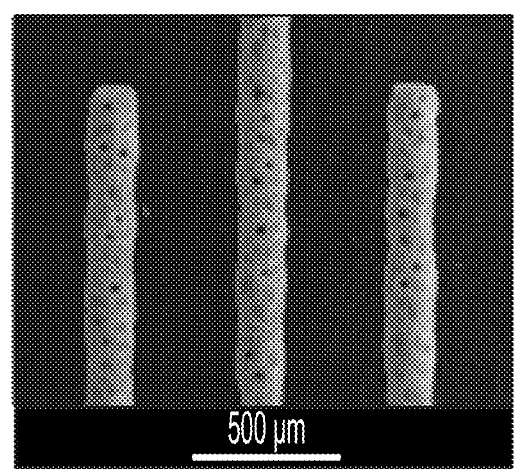
FIG. 3D

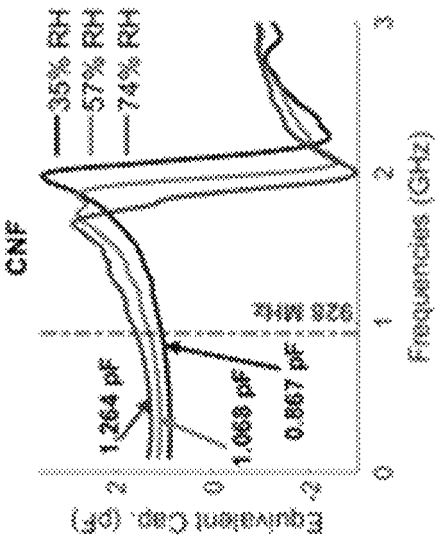
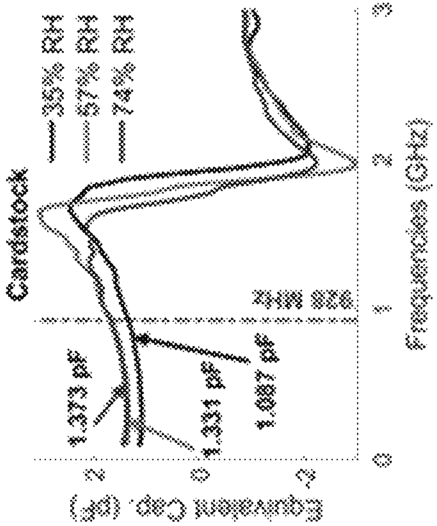
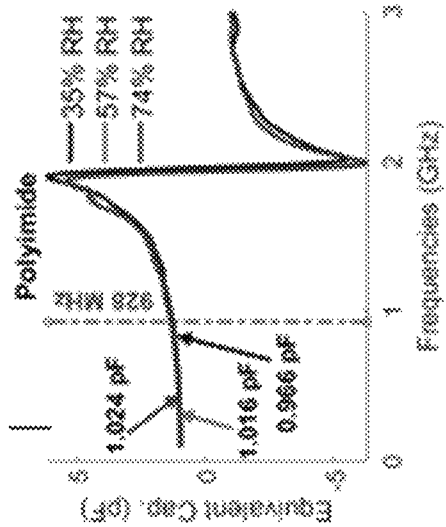
FIG. 6

Sensor coherently responds at a frequency determined by the capacitive sensor

Operational Principle of Passive Sensors

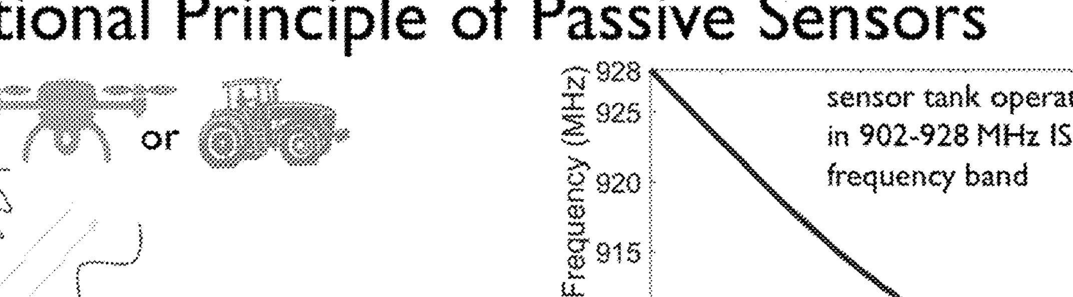

- sensor resonant frequency is determined by the vibrational frequency of a microresonator which is pulled by a sensor capacitance
- at the resonant frequency of the sensor tank circuit, the RF signal is stored for approximately 1μs, allowing nearby RF signal reflec...

FIG. 8

Screen-Printed Conductors on Biodegradable, Paper Substrates

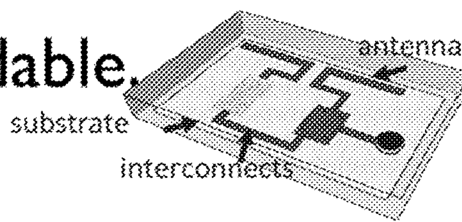

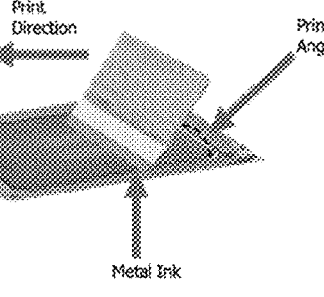

- Commercial Ag screen printing inks
- Sheet resistance of ~18 mΩ/sq

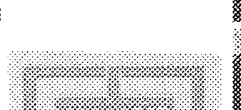
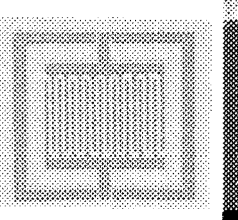
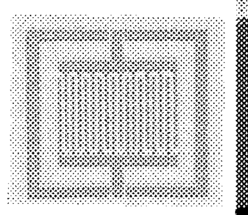
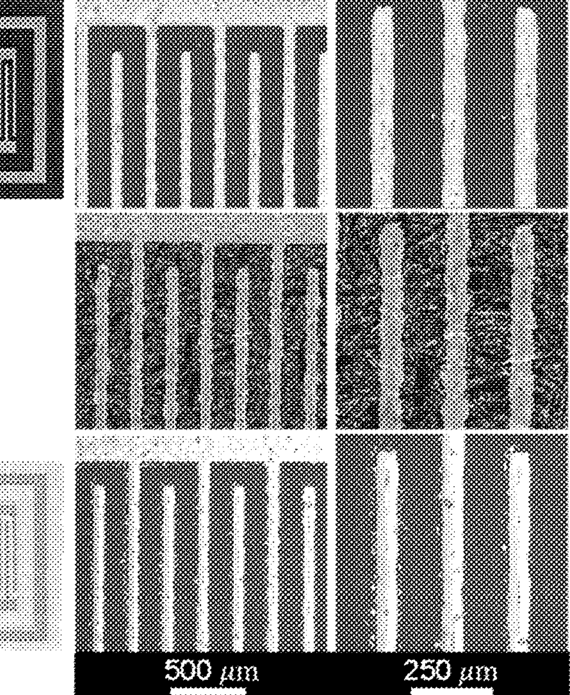

Polyimide
- Not biodegradable
- Low roughness (0.5 μm) allows printing of high quality RF traces

Cardstock
- Biodegradable
- High roughness (3.5 μm) prevents the realization of high quality RF structures

Cellulose Nanofibrils (CNF) infused Cardstock
- Biodegradable
- Low roughness (0.5 μm) allows formation of high performance RF structures (sensors and antennas)

FIG. 9

Low Cost, Passive Wireless Soil Moisture Sensors
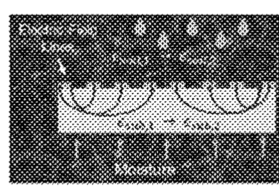
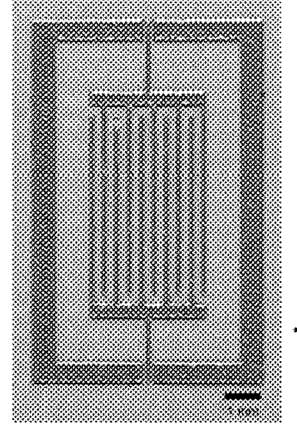
Capacitive wireless moisture sensor screen printed on CNF infused cardstock
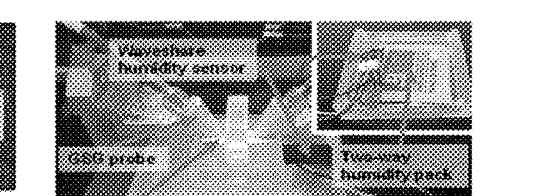
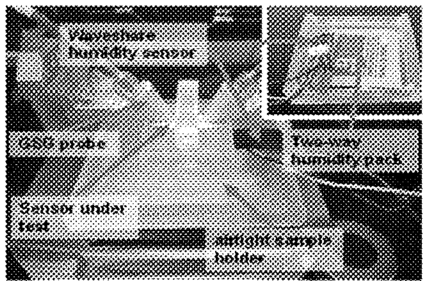
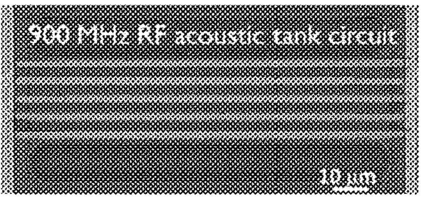
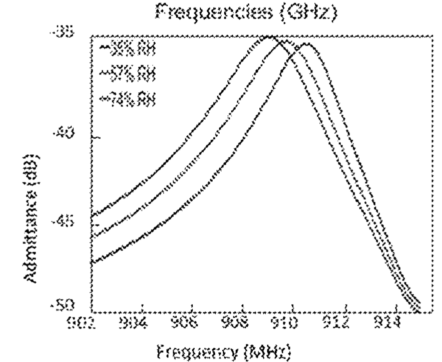
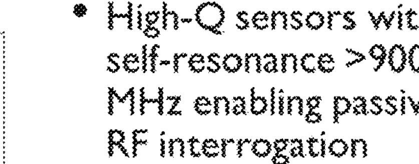
- High-Q sensors with self-resonance >900 MHz enabling passive RF interrogation
FIG. 10

Fixture

- Cardstock and CNF solution squeezed between plates of acrylic.
- All diffusion takes place to sides of fixture.

Drying Time decreased from 15+ hrs to 4 hrs.
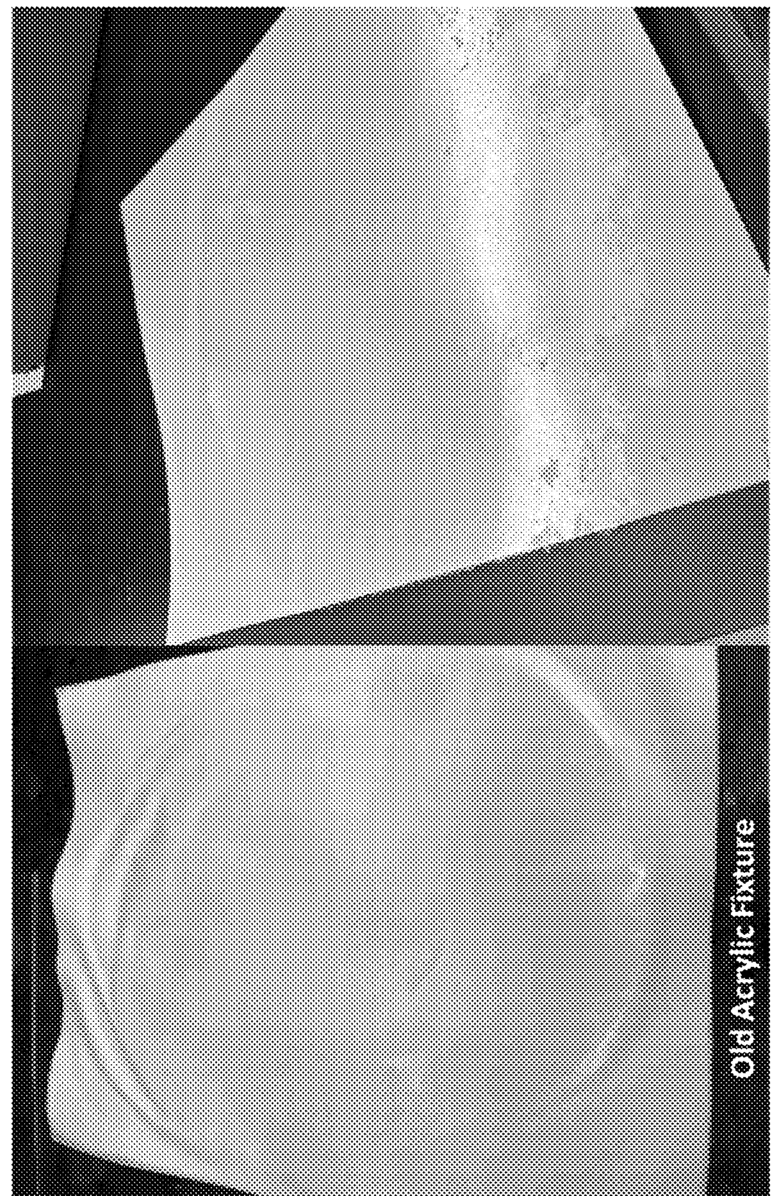
FIG. 23

Screen Printing Process
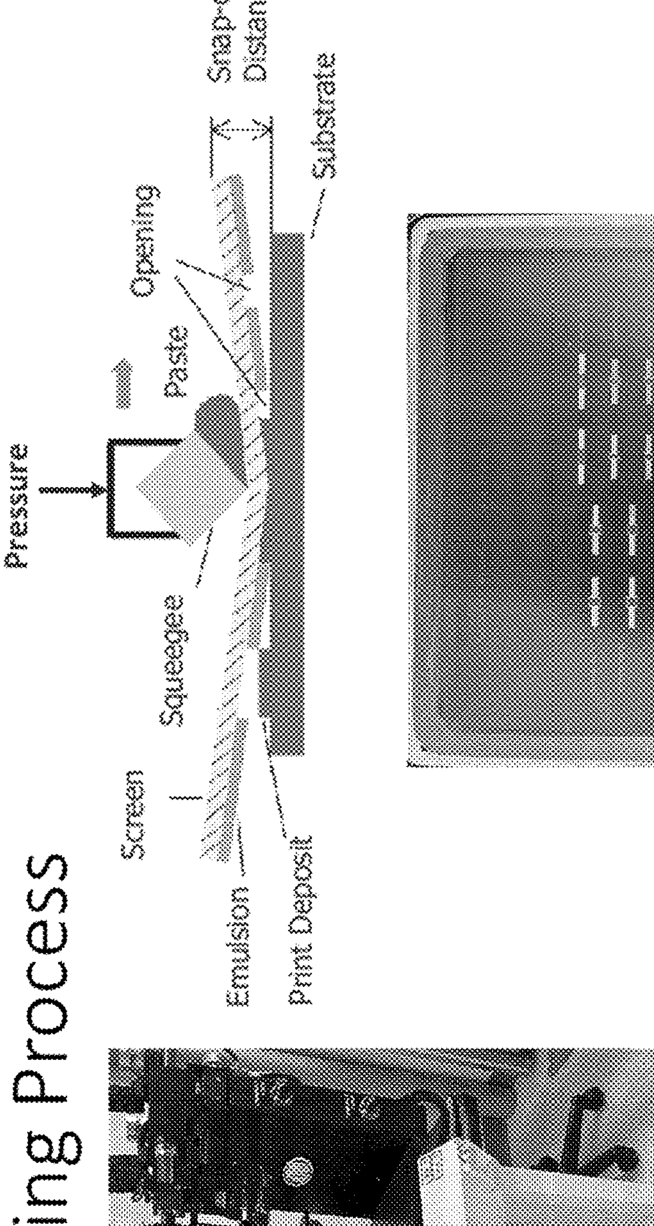
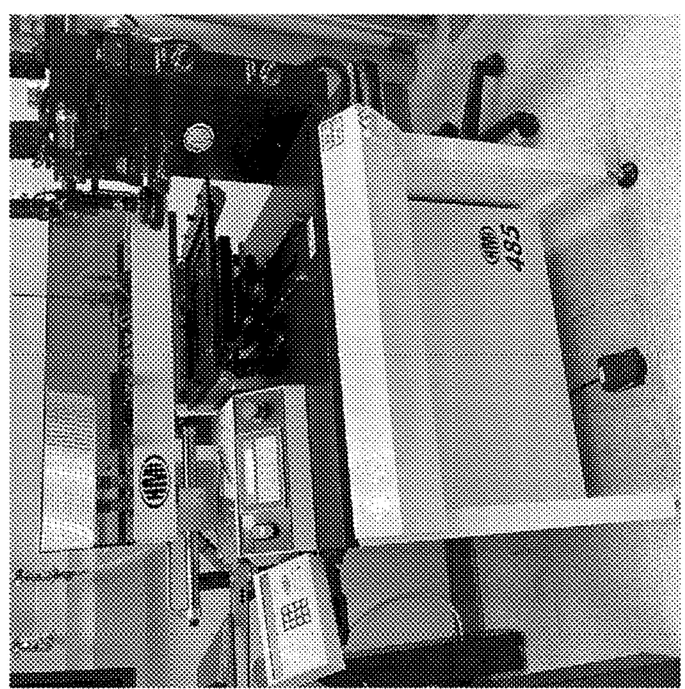
FIG. 24

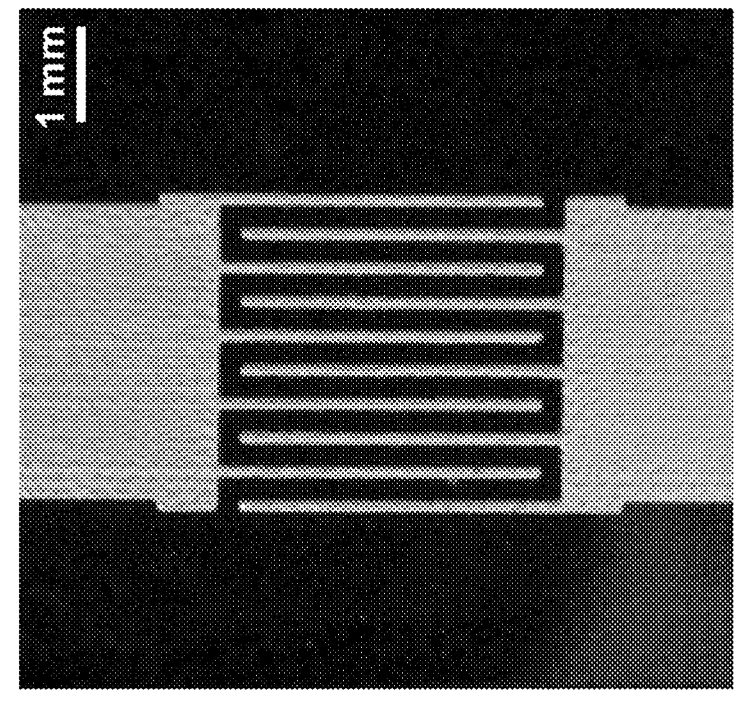
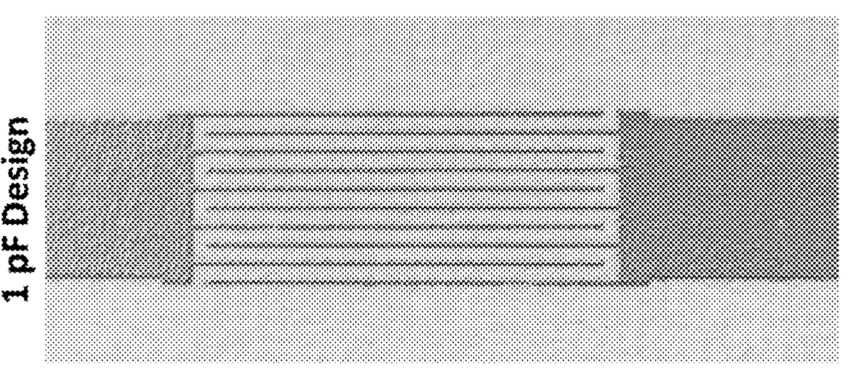
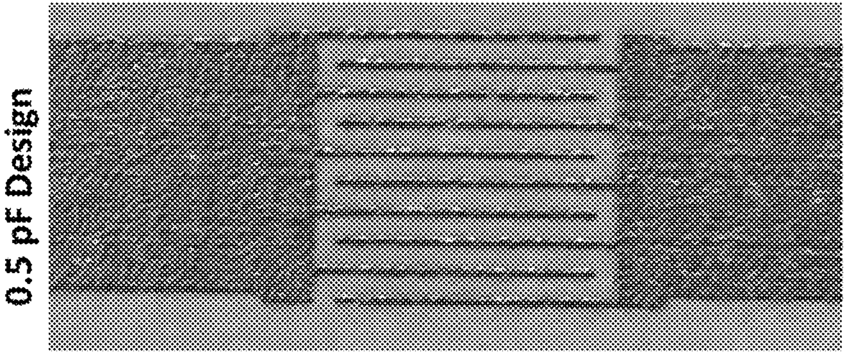
FIG. 25

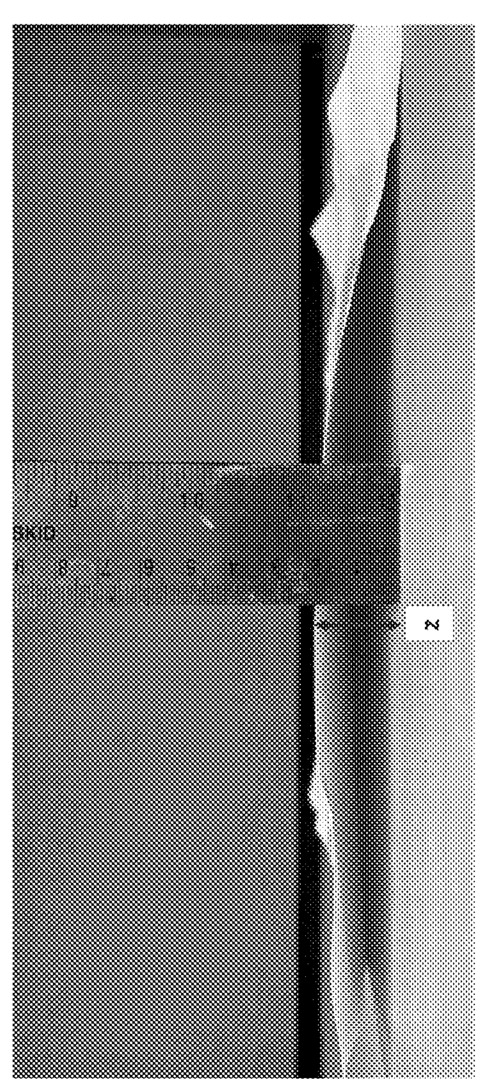
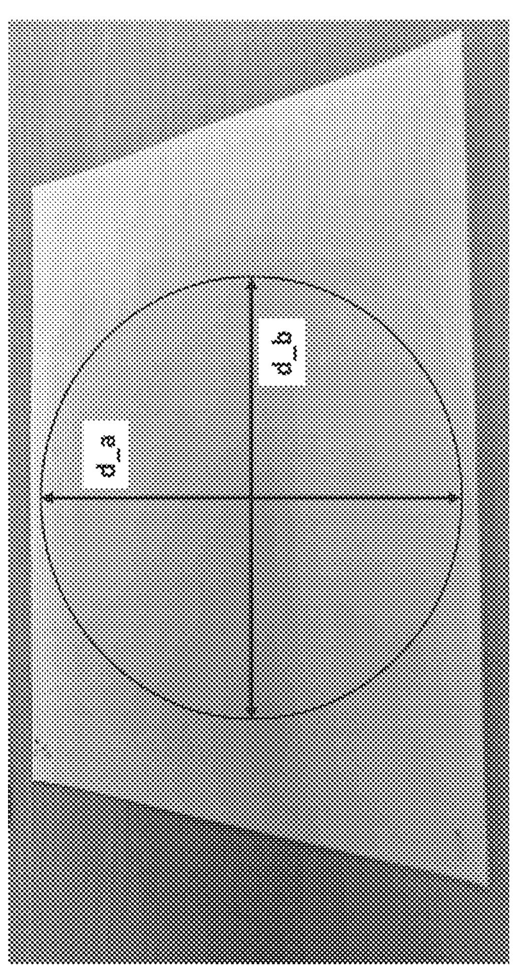
FIG. 26

SMOOTH AND BIODEGRADABLE NANO-CELLULOSE COMPOSITES FOR PRINTED ELECTRONICS

CROSS-REFERENCE TO RELATED APPLICATIONS

The present application claims priority to and the benefit of U.S. patent application Ser. No. 63/497,290, "Smooth And Biodegradable Nano-Cellulose Composites For Printed Electronics" (filed Apr. 20, 2023). All foregoing applications are incorporated herein by reference in their entireties for any and all purposes.

GOVERNMENT RIGHTS

This invention was made with government support under 1941529 awarded by the National Science Foundation and 2017-67021-26601 awarded by the National Institute of Food and Agriculture, and 23-JV-11111122-020 awarded by the Department of Agriculture Forest Service. The government has certain rights in the invention.

TECHNICAL FIELD

The present disclosure relates to the field of composite materials and to the field of biodegradable electronic components.

BACKGROUND

Flexible electronics have grown in their interest and popularity over the last decade, with applications in several fields from structural and personal health monitoring to use cases in medical and surgical procedures and in agricultural monitoring. Traditional flexible electronics, however, utilize polymer materials, such as polyimide, that are non-biodegradable. As such, there is a large quantity of waste generated from the use of these materials, which is an especially pertinent problem in the medical field (e.g. single-use devices) where there is already much waste generation from non-biodegradable and non-renewable materials. Additionally, in applications such as agricultural monitoring, the use of non-biodegradable materials is not ideal as it requires sensor retrieval to avoid negatively impacting soil quality and fertility. With the growth of the number of sensors in the field due to the Internet of Things (IoT), device retrieval can be very time, labor, and cost intensive. Accordingly, there is a long-felt need in the art for improved flexible electronics.

SUMMARY

By using the described approach, one can eliminate several of these issues. While other researchers have developed sensors on paper-based substrates before, the key differences between the disclosed material and others are at least biodegradability, substrate quality and fabrication cost. Due to the composite including cellulose, the material is biodegradable, helping to combat waste. Additionally, the exceptional surface smoothness that the CNF provides enables fabrication of structures with high precision and repeatability, making this material ideal for use in large scale manufacturing of sensors where quality assurance and repeatability is key. There exist paper-based substrates with high surface smoothness, but such substrates contain plastic and/or inorganic fillers, making them non-biodegradable. While CNF based substrates have been explored, all such materials are almost entirely made completely of CNF. While such CNF nanopapers do have favorable surface properties, they are costly to make and do not have mechanical robustness. By using a small amount of CNF and combining with a micro cellulose network, one can achieve both low cost and exceptional mechanical properties.

The present disclosure provides a composite, comprising: a first surface, a second surface, and a thickness between the first surface and the second surface, a porous scaffold having a plurality of pores extending from the first surface into the thickness, at least some of the plurality of pores being at least partially filled with cellulose nanofibrils, and the first surface of the composite having a root mean square (RMS) roughness of from about 0.01 to about 0.1 μm.

Also provided is a sensor module, the sensor module comprising a composite according to the present disclosure, for example, according to any one of Aspects 1-11, the sensor module optionally being configured as a moisture sensor.

Further provided is a method, comprising detecting a moisture level of a medium with a sensor module according to the present disclosure, for example according to any one of Aspects 12-13.

Additionally provided is a method, comprising: forming a composite having a first surface, a second surface, and a thickness therebetween by contacting (1) a solution of cellulose nanofibrils and (2) a porous scaffold having extending from a first surface of the scaffold, the contacting being performed such that at least some of the plurality of the pores are at least partially filled with cellulose nanofibrils of the solution and that the first surface of the composite has a root mean square roughness of from about 0.01 to about 0.1 μm, the solution optionally being applied through a stencil to the porous scaffold, optionally heating the solution of cellulose nanofibrils applied to the porous scaffold, and optionally compressing the porous scaffold after contacting the porous scaffold and the solution of cellulose nanofibrils.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various aspects discussed in the present document. In the drawings:

FIGS. 3A-3D provide comparative data illustrating the disclosed technology;

FIG. 6 provides comparative data illustrating the disclosed technology;

FIG. 8 provides an illustration of the disclosed technology;

FIG. 9 provides an illustration of the disclosed technology; and

FIG. 10 provides an illustration of the disclosed technology.

FIG. 11 (step 1) A sheet of cardstock is used as the base material. FIG. 11 (step 2) The cardstock is wet and pressed against a sheet of PMMA. FIG. 11 (step 3) CNF solution is then deposited on the center of the sheet and a second sheet of PMMA is pressed down with a uniform pressure of 560 Pa to spread the solution into a uniform layer. FIG. 11 (step 4) The pressed composite is dried to remove excess moisture and form the surface film.

(FIG. 15A—left side) Capacitance and (FIG. 15B—right side) phase angle values for small (0.5 pF) and large (1 pF) interdigitated capacitive structures printed on polyimide, NCIP, and cardstock. Each data point represents the average value calculated from five individual samples. Capacitance and phase angle measurements were done using a LCR meter at a frequency of 8 MHz.

(FIG. 17A—top row) Average moisture uptake and release curves for NCIP samples cycled between 55% and 85% RH (Δ 30% RH) calculated from 3 individual samples. The Parallel Exponential Kinetics (PEK) model is used to fit both the (FIG. 17B) moisture uptake and (FIG. 17C) moisture release curves and extract relevant time constants.

FIG. 23 provides a comparison of results obtained with a fixture according to FIG. 20 ("Old Acrylic Fixture") and with a fixture according to FIG. 21 ("New Aluminum Fixture").

FIG. 24 provides an exemplary screen printing process.

FIG. 25 provides exemplary features made on a cardstock substrate, a nano cellulose infiltrated paper (NCIP) substrate, and a polyimide substrate.

FIG. 26 provides an illustration of the measurements made in connection with the data shown in Tables 5.

DETAILED DESCRIPTION OF ILLUSTRATIVE EMBODIMENTS

Figure 1:
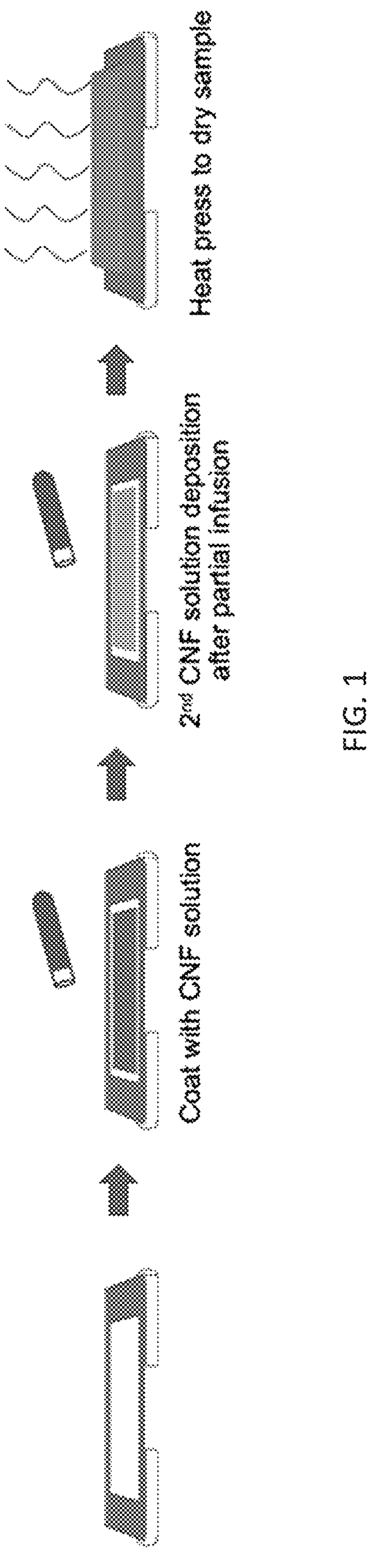
FIG. 1 provides a non-limiting depiction of a process for fabricating a composite according to the present disclosure.

The present disclosure may be understood more readily by reference to the following detailed description of desired embodiments and the examples included therein.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing. All publications, patent applications, patents and other references mentioned herein are incorporated by reference in their entirety. The materials, methods, and examples disclosed herein are illustrative only and not intended to be limiting.

The singular forms "a," "an," and "the" include plural referents unless the context clearly dictates otherwise.

As used in the specification and in the claims, the term "comprising" can include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any impurities that might result therefrom, and excludes other ingredients/steps.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

Unless indicated to the contrary, the numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently of the endpoints. The endpoints of the ranges and any values disclosed herein are not limited to the precise range or value; they are sufficiently imprecise to include values approximating these ranges and/or values.

As used herein, approximating language can be applied to modify any quantitative representation that can vary without resulting in a change in the basic function to which it is related. Accordingly, a value modified by a term or terms, such as "about" and "substantially," may not be limited to the precise value specified, in some cases. In at least some instances, the approximating language can correspond to the precision of an instrument for measuring the value. The modifier "about" should also be considered as disclosing the range defined by the absolute values of the two endpoints. For example, the expression "from about 2 to about 4" also discloses the range "from 2 to 4." The term "about" can refer to plus or minus 10% of the indicated number. For example, "about 10%" can indicate a range of 9% to 11%, and "about 1" can mean from 0.9-1.1. Other meanings of "about" can be apparent from the context, such as rounding off, so, for example "about 1" can also mean from 0.5 to 1.4. Further, the term "comprising" should be understood as having its open-ended meaning of "including," but the term also includes the closed meaning of the term "consisting." For example, a composition that comprises components A and B can be a composition that includes A, B, and other components, but can also be a composition made of A and B only. Any documents cited herein are incorporated by reference in their entireties for any and all purposes.

Any embodiment or aspect provided herein is illustrative only and does not limit the scope of the present disclosure or the appended claims. Any part or parts of any one or more embodiments of aspects can be combined with any part or parts of any one or more other embodiments or aspects.

The present disclosure relates, in some aspects, to a novel cellulose-based composite paper, which has high surface smoothness and low porosity, as well as a process for its fabrication. This composite consists of a standard paper substrate that is coated with a thin layer of TEMPO-oxidized cellulose nanofibril (CNF) solution. The CNF solution partially infiltrates the paper substrate and bonds strongly to the paper via hydrogen bonding. The solution is coated onto the surface of the cardstock and then subsequently pressed to form highly smooth and dense surface. This invention allows printed electronics with small feature sizes to be printed on cellulose-based substrates, facilitating the fabrication of biodegradable sensors and electronics. Typically printed electronics are fabricated on polymer substrates or papers with polymer coatings/fillers.

Example Fabrication

The following is an example, non-limiting method of fabricating a composite according to the present disclosure. An example solution was prepared from a 1.47 mmol COONa/g dry CNF in Sodium form that has been mixed with water to create a 0.99 wt % CNF gel. To prepare the coating solution, the CNF gel is combined with deionized water in a 1:1 ratio to form a 0.5 wt % mixture. This mixture is then magnetically stirred at 500 RPM for 30 minutes to uniformly mix the CNF with the deionized water and prepare a homogeneous solution. The solution is then centrifuged at 3000 RPM for 3 minutes to ensure that cellulose nanofibril strands do not agglomerate and are uniformly dispersed. The solution is then stored in a fridge at −5° C. for at least 12 hours prior to use. The viscosity of the CNF solution is dependent on the stability of the cellulose network. Heat can disrupt and damage the network and change the viscosity. To avoid this and to make sure that the viscosity is uniform from sample to sample, the prepared solution can be stored in a cold environment and time is provided to allow the network to reform after the preparation process.

Two example methods for preparing the disclosed composites are detailed below. For method number one (FIG. 1), which one can call the 'stencil method', a two piece PMMA stencil is fabricated. A 6"×6" backing piece and a 6"×6" frame with a 4"×4" rectangular aperture are both laser cut out of ⅛" PMMA. To prepare the composite, a sheet of A4 cardstock (obtained from Neenah paper) is cut into a 6"×6" piece and wet evenly and pressed flat against the backing layer. The paper can be wet to allow the porous structure of the cardstock to open up so that the CNF solution can infuse well into the surface. Wetting the paper can minimizes any drying deformation that might occur since having a composite that is uniformly wet will encourage a uniform drying gradient. The frame is then clamped over the backing piece to sandwich the cardstock between the two—one can use binder clips, one on each side of the stencil, for the clamping. 12.5 grams of the CNF solution is evenly coated on the surface of the cardstock and allowed to partially infuse for approximately 1.5 hours before a second coating is applied. During the infusion step, water evaporates from the solution, concentrating the CNF. After partial infiltration of the second layer, a ⅛" 3.9"×3.9" PMMA piece is placed over the rectangular aperture and the sample is heat pressed at 60° C. for 20 minutes to form the surface layer and then oven dried at 60° C. for 12 hours to remove any remaining moisture. Below is a schematic of the process flow of the 'stencil method'.

Figure 2:
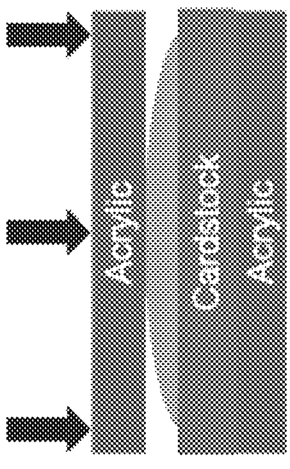
FIG. 2 provides a non-limiting depiction of a process for fabricating a composite according to the present disclosure.

For the second preparation method, which one can call the 'pressing method' (FIG. 2), two ¼" 6"×6" laser cut PMMA pieces are used. As in the 'stencil method', a sheet of A4 cardstock (obtained from Neenah paper) is cut into a 6"×6" piece and wet evenly and pressed flat against the backing layer for the same purposes as detailed above, 7 grams of CNF solution are deposited into the center of the wet cardstock and the second piece of PMMA is brought down parallel to the surface of the cardstock and pressed to evenly distribute the CNF solution into a thin and continuous layer. Depositing the CNF solution in the center in one mound is key as without this step, air bubbles are very likely to form during the pressing step, leading to a patchy and uneven final product.

After pressing the second piece into contact, a sheet of stock aluminum is placed on top to ensure that the PMMA sheets are flat and maintain uniform contact with the cardstock sheet. The main difference between this method and the 'stencil method' is that one can directly press the CNF solution without allowing for the partial infusion step. By using less CNF solution, one can press the composite immediately and allow for the drying and infiltration to occur simultaneously. Below is a schematic of the process flow of the pressing method'

It should be noted that while the stencil method here was detailed for a 6"×6" sample, the method can easily be scaled up to fabricate larger samples using the same steps.

Surface Properties

This disclosed CNF composite demonstrates both exceptional surface smoothness and moisture response, properties that make it an excellent candidate substrate for printed electronics. Its exceptional surface smoothness allows for the fabrication of repeatable and consistent electrical structures with small feature sizes. To evaluate this SEM images were taken of silver capacitive structures screen printed on cardstock, polyimide, a commonly used polymer substrate in flexible electronics, and the CNF composite. This is shown in FIGS. 3A-3D, with (FIG. 3A) showing structures printed on cardstock, (FIG. 3B and FIG. 3C) showing structures printed on polyimide, and (FIG. 3D) showing structures on the CNF composite. The traces printed on polyimide and CNF composite are qualitatively superior to the structures printed on cardstock.

Figures 4A, 4B:
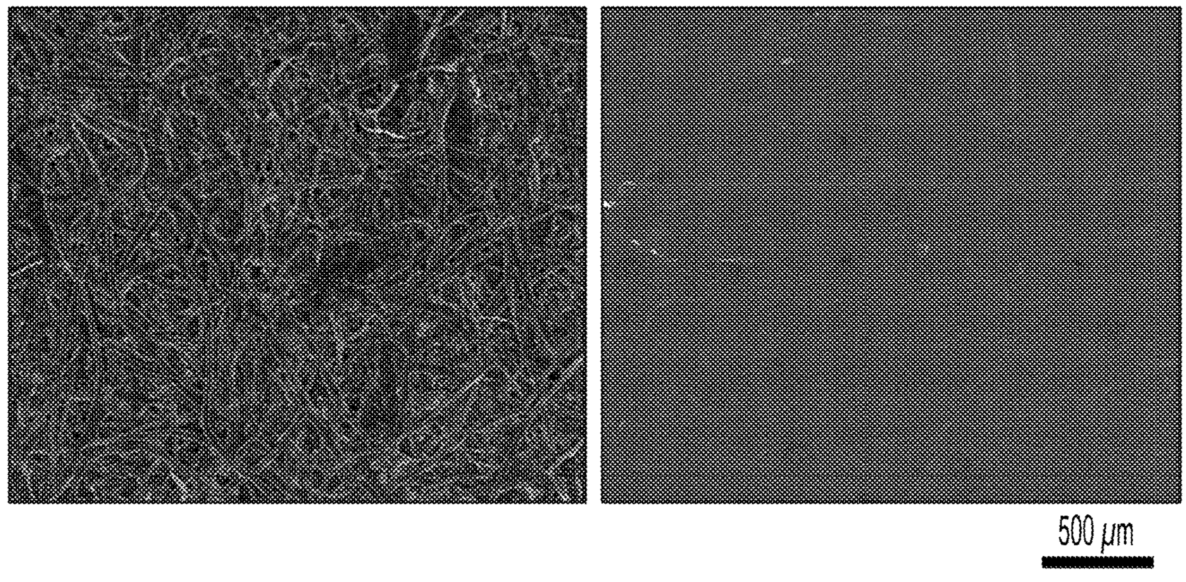
FIGS. 4A-4B provide comparative data illustrating the disclosed technology.

The traces on the cardstock exhibit greater non-uniformity and edge roughness due to the porosity and roughness of the surface. The high porosity leads to uneven ink infiltration, while the micro scale fibers create a non-planar surface. Both of these contribute to poor trace quality and variation in the thickness of the traces. Infusion of nanocellulose onto the cardstock surface helps us solve this problem. The nanocellulose is able to fill in the surface pores and create a smooth and uniform surface. This can clearly be seen from the SEM images of the cardstock and CNF composite surfaces shown in FIG. 4A and FIG 4B. In FIG 4A, it can be seen that the microcellulose network of the cardstock leads to a highly porous network. Introduction of the nanocellulose fills these pores and results in the smooth surface seen in FIG. 4B.

Figure 5:
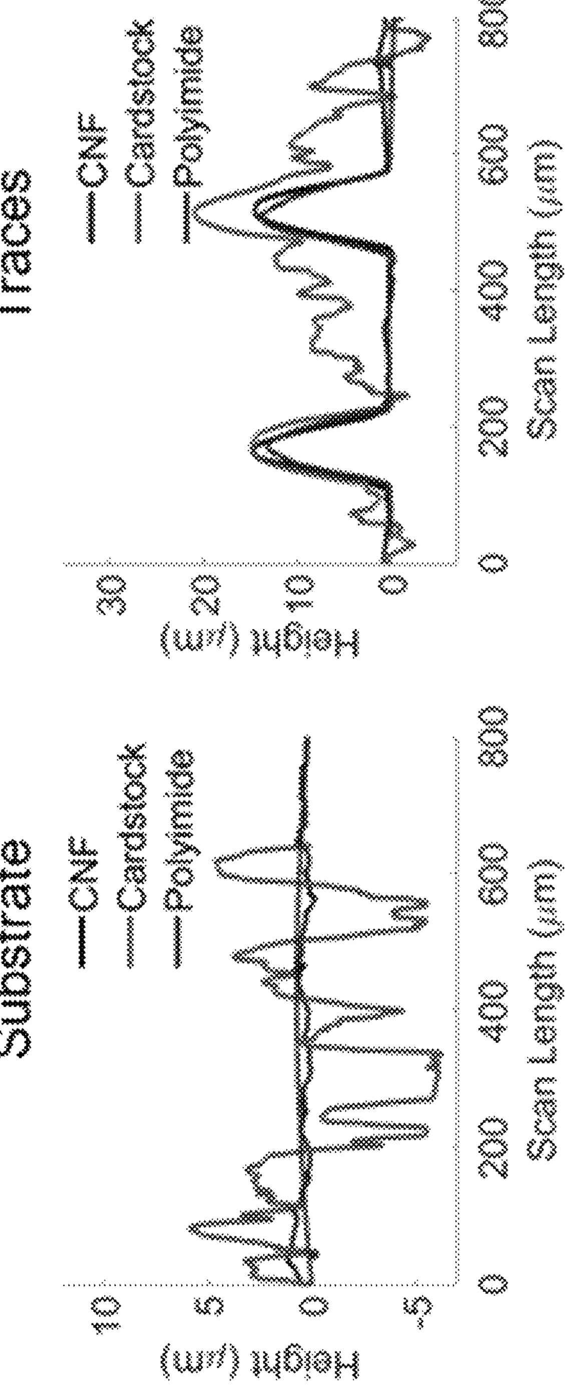
FIG. 5 provides comparative data illustrating the disclosed technology.

In addition to SEM imaging, surface profilometry was used to quantify the roughness of the substrates as well as the quality of the printed traces. The surface profilometry traces for each substrate are shown in FIG. 5. The root mean square (RMS) roughness was calculated for each substrate, with the CNF-composite and polyimide exhibiting RMS roughnesses of 0.52 μm and 0.47 μm respectively while the RMS roughness of the cardstock was nearly an order of magnitude larger at 3.5 μm. This difference in the surface roughness is expected since the surface of the cardstock is comprised of microscale cellulose fibers. The surface roughness of each substrate directly correlated to the quality and consistency of the structures printed on them. Traces printed on the CNF-composite and polyimide, both low roughness substrates, had average trace heights and standard deviations of 13±2.6 μm and 14±1.1 μm while the cardstock structures exhibited greater variability with an average height and standard deviation of 15.1±6.1 μm.

Moisture Response

The presence of nanocellulose in this composite material allows for it to respond to changes in moisture content in the environment, allowing for it to be used as both a humidity and soil moisture sensor. Nanocellulose, specifically CNFs in our case, are highly hygroscopic, meaning that they readily absorb and adsorb moisture due to the presence of free hydroxyl groups. Moreover, they can be used as wireless RF sensors due to their excellent electrical response in the Industrial Scientific and Medical (ISM) frequency band, which are radio wave bands allocated for industrial use. Here, the ISM band one can utilize is the Region 2 band (902-928 MHz), which is the band reserved for North and South America. Shown in FIG. 6 is the frequency dependent (0-3 GHz) equivalent capacitance of capacitive structures printed on polyimide, cardstock, and the CNF composite under various moisture conditions.

One can note that the structures printed on polyimide show little to no response as polyimide is not moisture responsive, but see a humidity dependence change in the equivalent capacitance for both the cardstock and CNF capacitors. However, one can see that the structures on CNF composite exhibit a 45.8% increase in capacitance compared to a 26.3% increase for structures cardstock over a 39% change in RH meaning that it demonstrates greater sensitivity. Additionally, one can note that the self resonance response of the structures printed on the CNF composite is well above our band of operation, meaning that one can directly extract the capacitance change as a function of moisture content from the electrical data. One can also note that the self impedance of the structures printed on the CNF composite are 40% lower than those printed on cardstock, which translates to a higher Q factor and therefore greater sensor performance.

Figure 7:
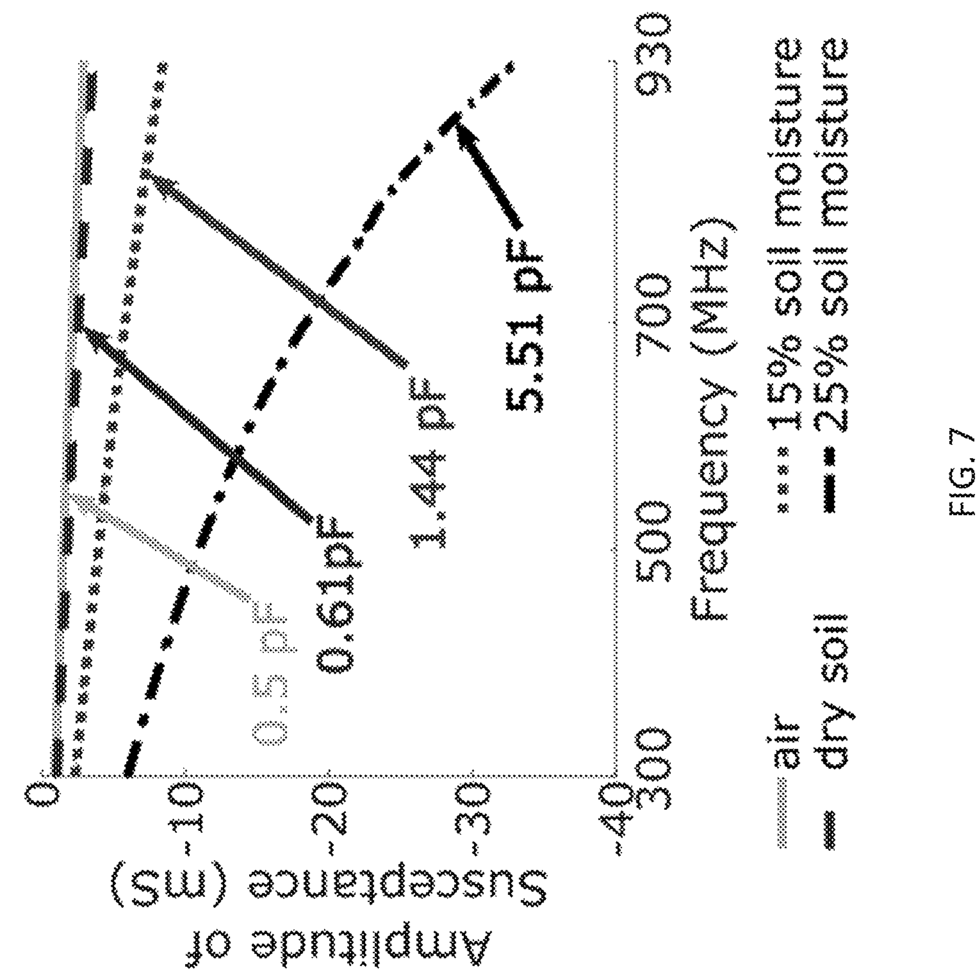
FIG. 7 provides comparative data illustrating the disclosed technology.

Also demonstrated is the ability to use this moisture response property in subsurface soil environments for moisture sensing. Shown in FIG. 7 is the amplitude of the susceptance of a capacitive sensor printed on the CNF composite under various moisture conditions in loamy sand.

One can note that the sensor is responsive over a soil moisture range of 0-25% soil moisture, with 25% being the saturation moisture percentage (i.e. maximum amount of water that a soil type can hold) for loamy sand soil. As such, one can see that sensors fabricated on this CNF composite material are capable of sensing over the full moisture range for such soil types. Loamy sand soils are used for growing a variety of crops and so sensing platforms developed on this material would be capable of successfully characterizing soil moisture during the cultivation of such crops.

FIG. 8 provides an example depiction of the operational principle of a passive sensor according to the present disclosure.

FIG. 9 provides an example depiction of the operational principle of a passive sensor according to the present disclosure.

FIG. 10 provides an example depiction of the operational principle of a passive sensor according to the present disclosure.

Figure 11:
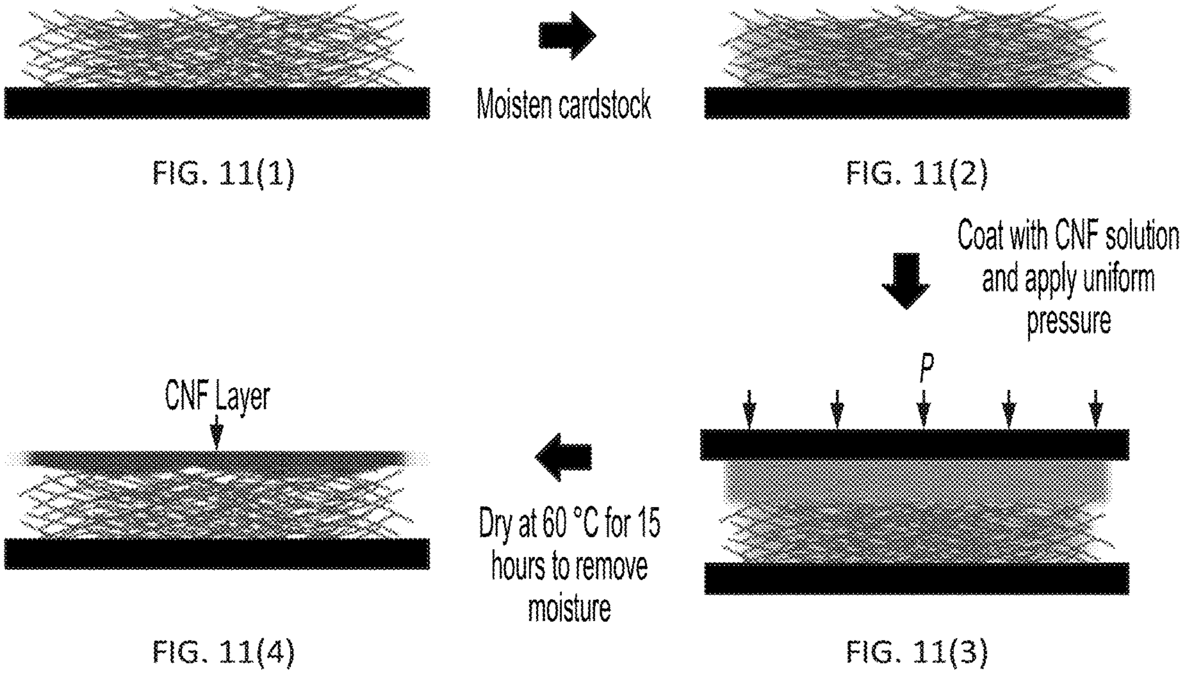
FIG. 11 provides a schematic of the NCIP fabrication process.

FIG. 11 provides a schematic of the NCIP fabrication process: Step 1) A sheet of cardstock is used as the base material. Step 2) The cardstock is wet and pressed against a sheet of PMMA. Step 3) CNF solution is then deposited on the center of the sheet and a second sheet of PMMA is pressed down with a uniform pressure of 560 Pa to spread the solution into a uniform layer. Step 4) The pressed composite is dried to remove excess moisture and form the surface film.

Figure 12A:
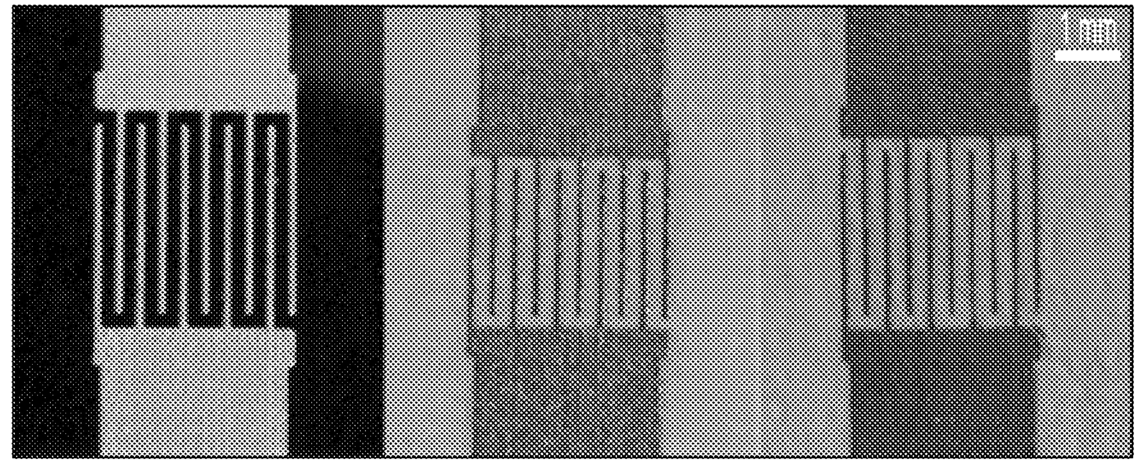
FIGS. 12A-12B: Optical microscope images of the FIG. 12A 0.5 pF capacitor (small) and FIG. 12B 1 pF capacitor (large) screen printed on polyimide, cardstock, and NCIP (left to right)
Figure 12B:
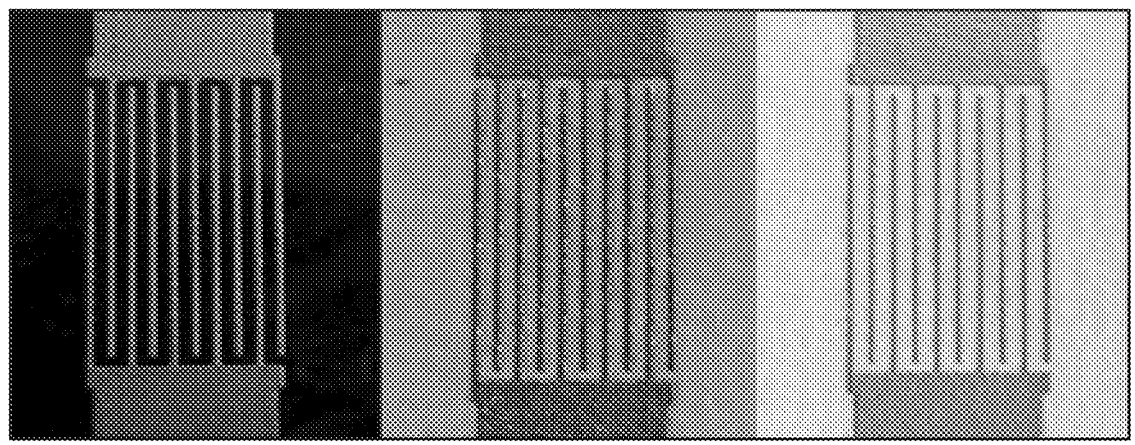

FIGS. 12A-12B provide optical microscope images of the (FIG. 12A) 0.5 pF capacitor (small) and (FIG. 12B) 1 pF capacitor (large) screen printed on polyimide, cardstock, and NCIP (left to right)

Figures 13A, 13B, 13C:
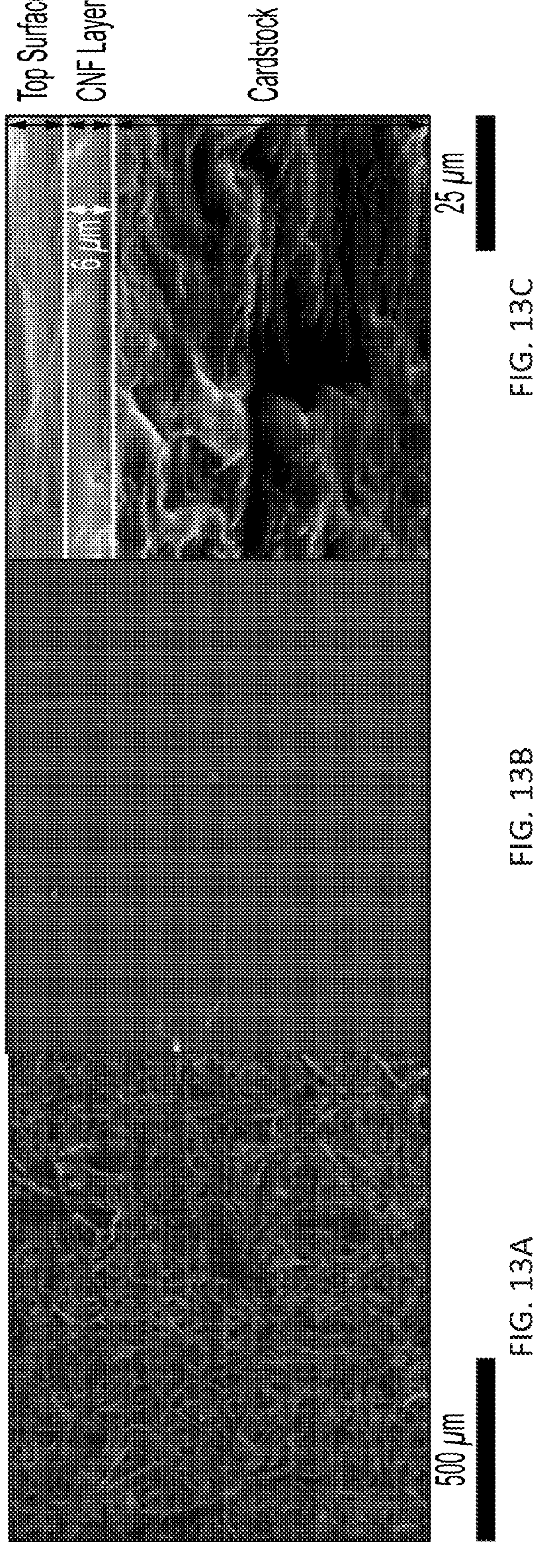
FIGS. 13A-13C: SEM images of the surfaces of (FIG. 13A) cardstock and (FIG. 13B) CNF-composite as well as a cross sectional SEM image of a Nanocellulose Infiltrated Paper (NCIP) (FIG. 13C). The surface is comprised of a thin layer of CNF approximately 5-7 μm thick that sits on top of a cardstock scaffold. The CNF layer planarizes and densifies the surface of the cardstock by filling in the surface pores of the microcellulose network in (FIG. 13A) resulting in the planarized surface in (FIG. 13B).

FIGS. 13A-13C provide SEM images of the surfaces of (FIG. 13A) cardstock and (FIG. 13B) CNF-composite as well as a cross sectional SEM image of a Nanocellulose Infiltrated Paper (NCIP) (FIG. 13C). The surface is comprised of a thin layer of CNF approximately 5-7 μm thick that sits on top of a cardstock scaffold. The CNF layer planarizes and densifies the surface of the cardstock by filling in the surface pores of the microcellulose network in (FIG. 13A) resulting in the planarized surface in (FIG. 13B).

Figures 14A, 14B, 14C:
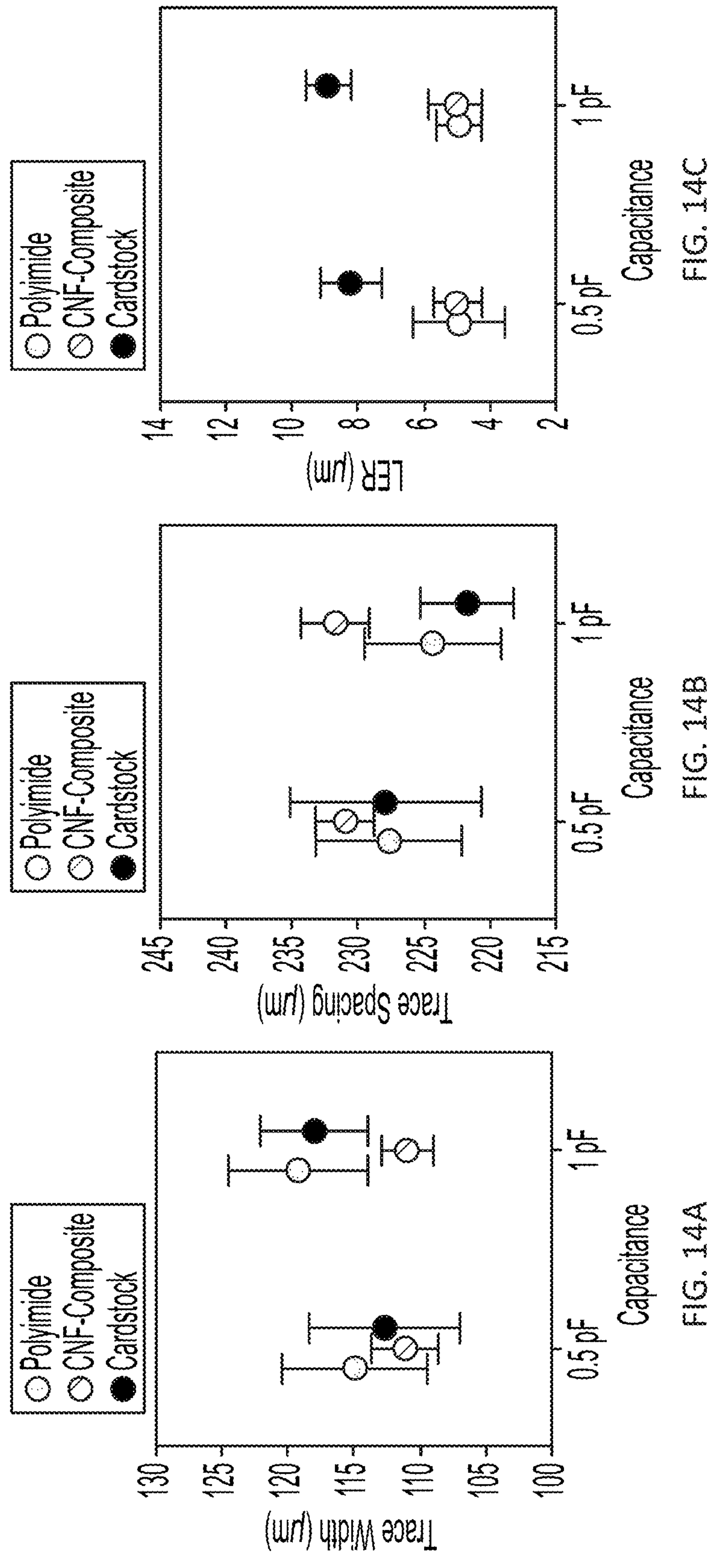
FIGS. 14A-14C: Average (FIG. 14A) trace widths and (FIG. 14B) trace spacing and (FIG. 14C) LER for small and large capacitive structures printed on polyimide, NCIP, and cardstock. Each data point represents the average calculated from 25 images.
Figures 15A, 15B, 15C, 15D:
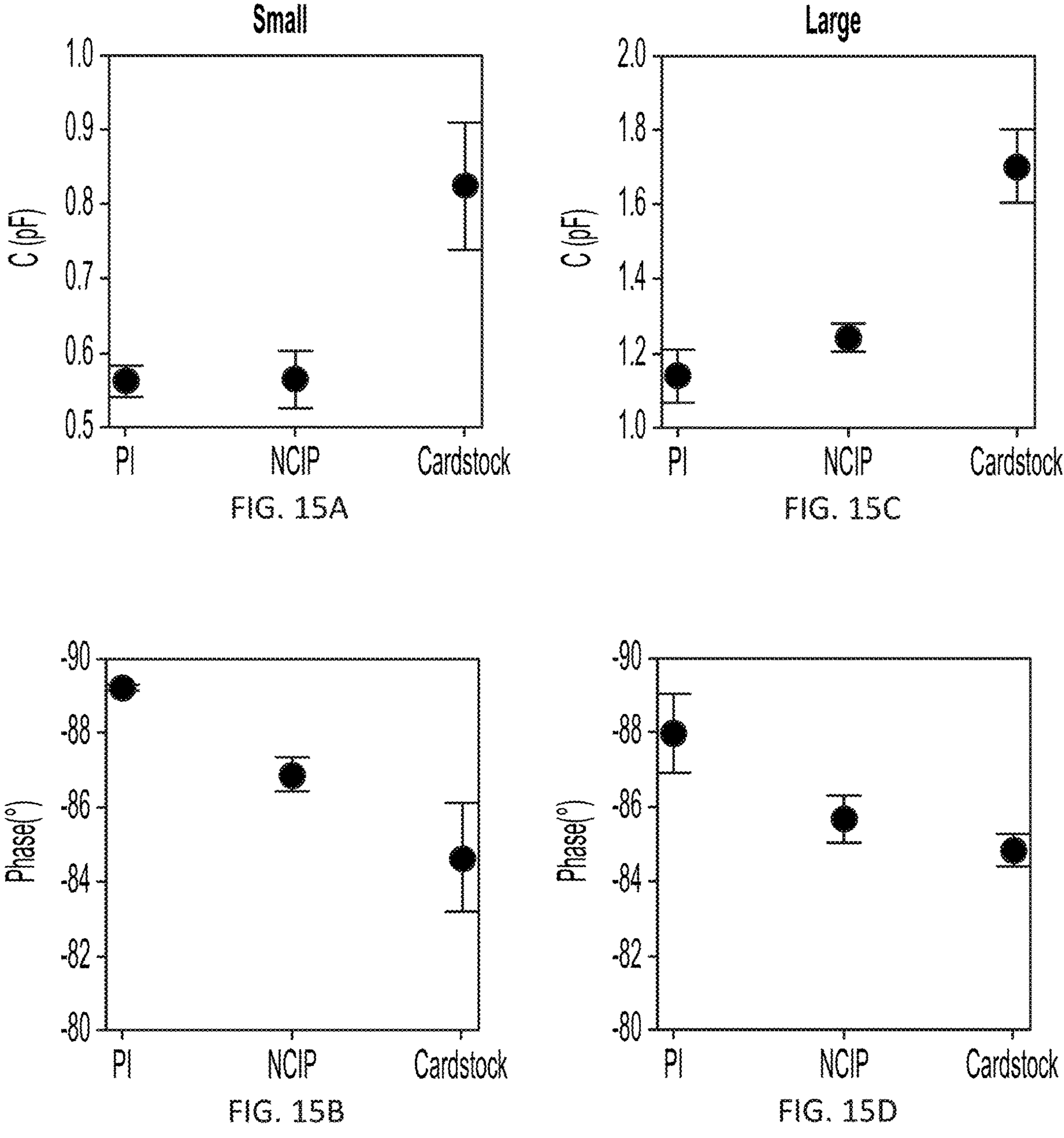
FIGS. 15A-15D.

FIGS. 14A-14C provide average (FIG. 14A) trace widths and (FIG. 14B) trace spacing and (FIG. 14C) LER for small and large capacitive structures printed on polyimide, NCIP, and cardstock. Each data point represents the average calculated from 25 images.

FIGS. 15A-15D provide (FIG. 15A—left side) Capacitance and (FIG. 15B—right side) phase angle values for small (0.5 pF) and large (1 pF) interdigitated capacitive structures printed on polyimide, NCIP, and cardstock. Each data point represents the average value calculated from five individual samples. Capacitance and phase angle measurements were done using a LCR meter at a frequency of 8 MHz.

Figure 16B:
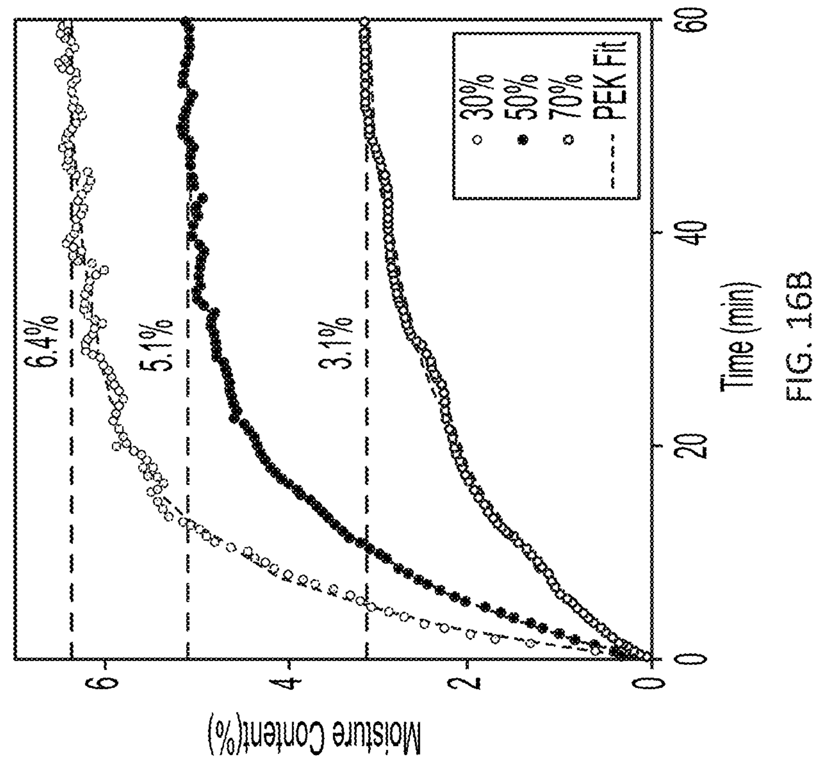
FIGS. 16A-16B: Moisture uptake data for (FIG. 16A) cardstock samples and (FIG. 16B) CNF-composite samples at 30%, 50%, and 70% relative humidity (RH). Each curve represents the average uptake for each RH condition calculated from three individual samples. The dashed black line is the fit to the moisture uptake data using the Parallel Exponential Kinetics (PEK) model.
Figure 16A:
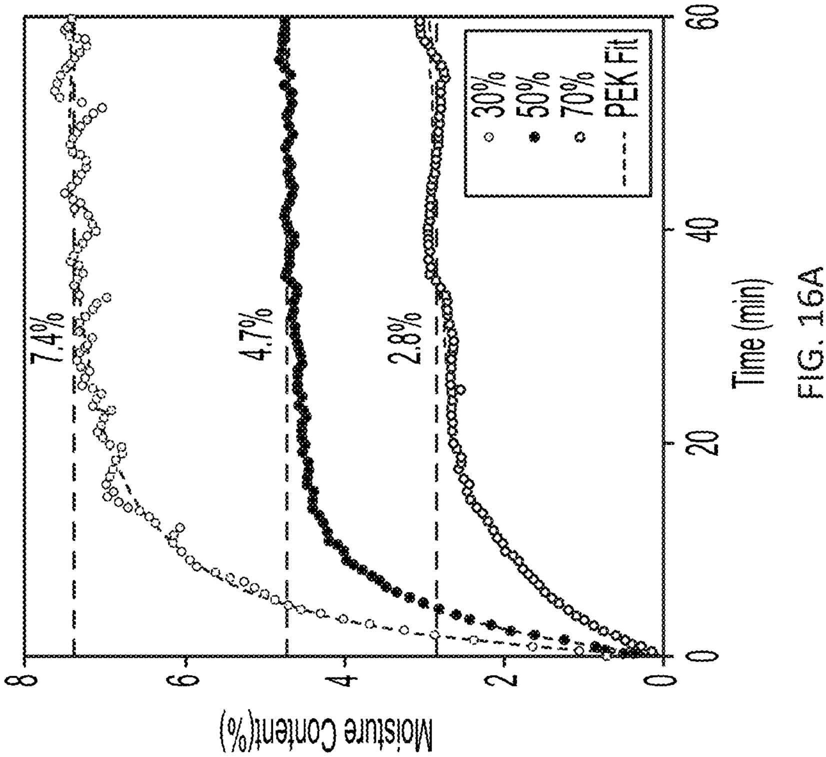

FIGS. 16A-16B provide Moisture uptake data for (FIG. 16A) cardstock samples and (FIG. 16B) CNF-composite samples at 30%, 50%, and 70% relative humidity (RH). Each curve represents the average uptake for each RH condition calculated from three individual samples. The dashed black line is the fit to the moisture uptake data using the Parallel Exponential Kinetics (PEK) model.

Figures 17A, 17B, 17C:
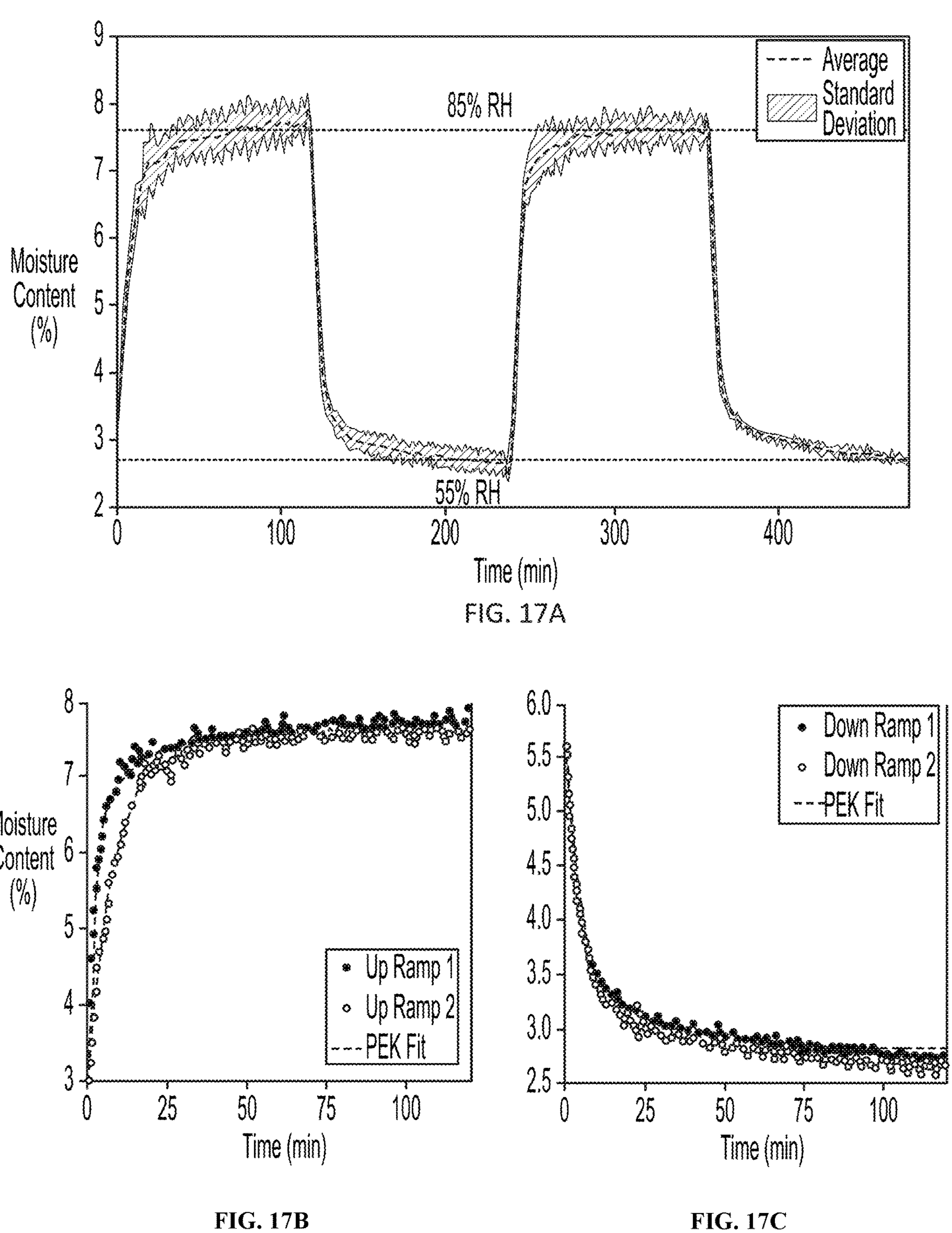
FIGS. 17A-17C.

FIGS. 17A-17C: (FIG. 17A) provide average moisture uptake and release curves for NCIP samples cycled between 55% and 85% RH (Δ30% RH) calculated from 3 individual samples. The Parallel Exponential Kinetics (PEK) model is used to fit both the (FIG. 17B) moisture uptake and (FIG. 17C) moisture release curves and extract relevant time constants.

Figure 18:
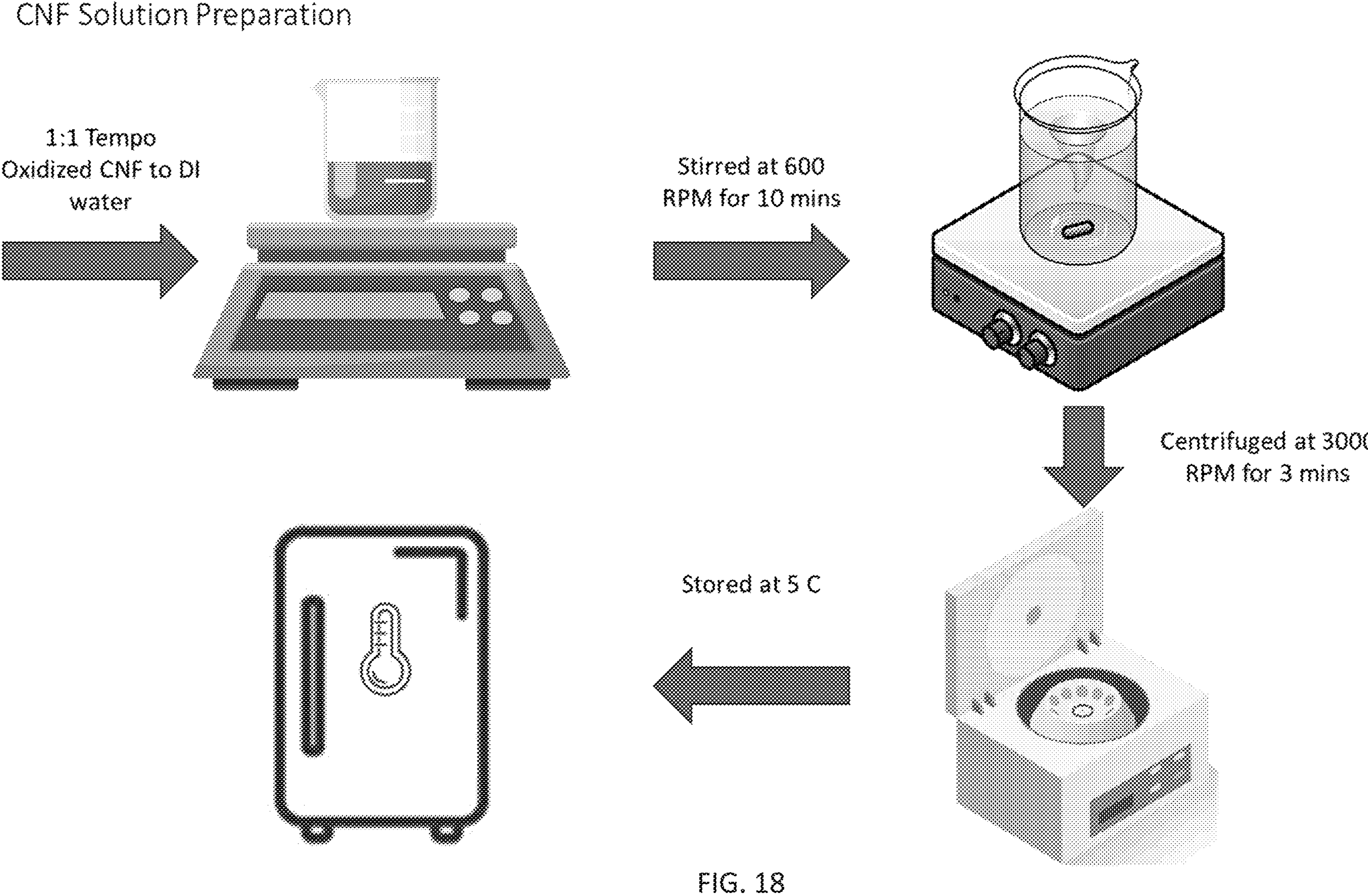
FIG. 18 provides an example process for CNF solution preparation.

FIG. 18 provides an example process for CNF solution preparation.

Figure 19:
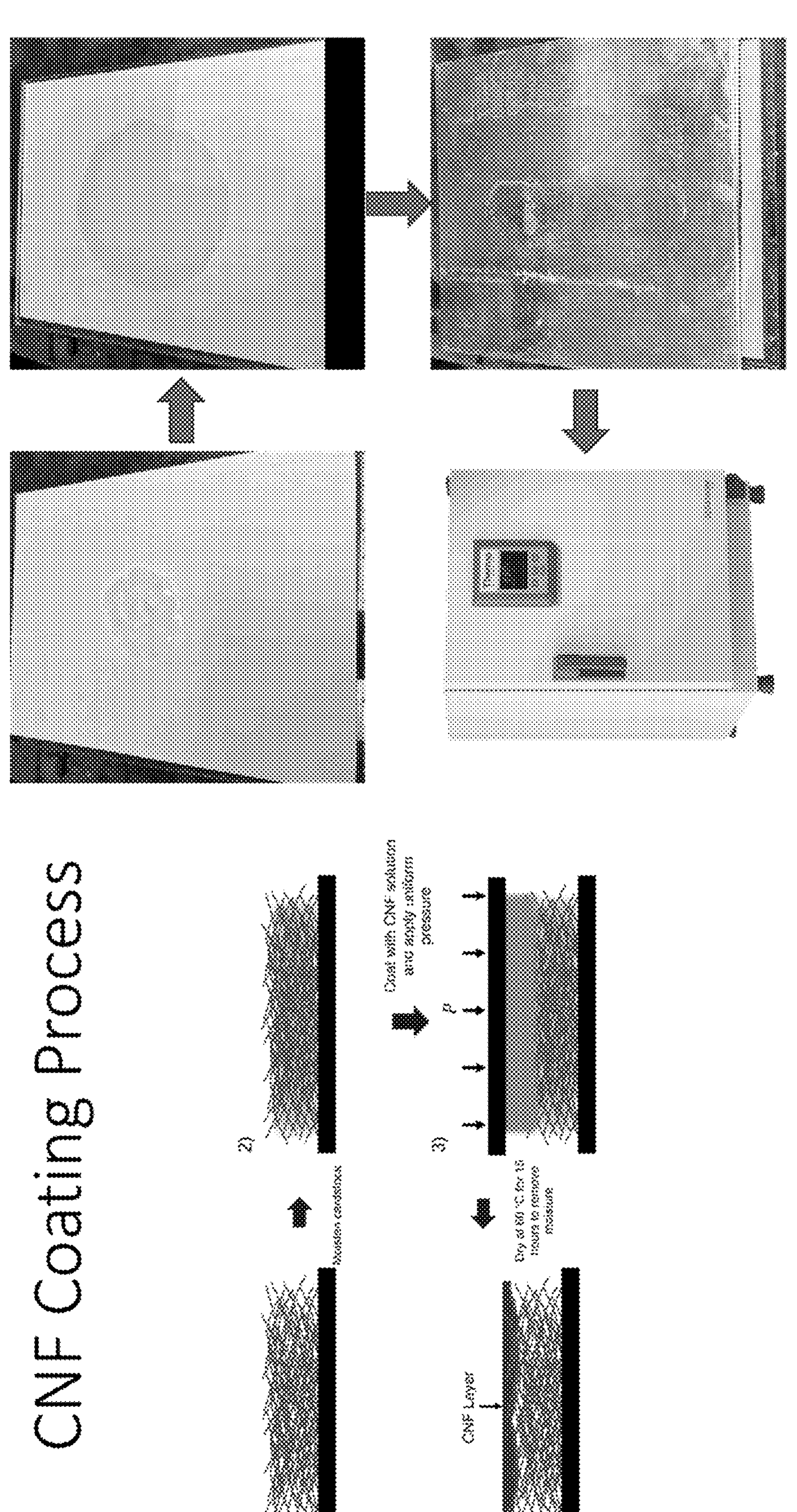
FIG. 19 provides an example process for placing a CNF coating onto cardstock.

FIG. 19 provides an example process for placing a CNF coating onto cardstock.

Figure 20:
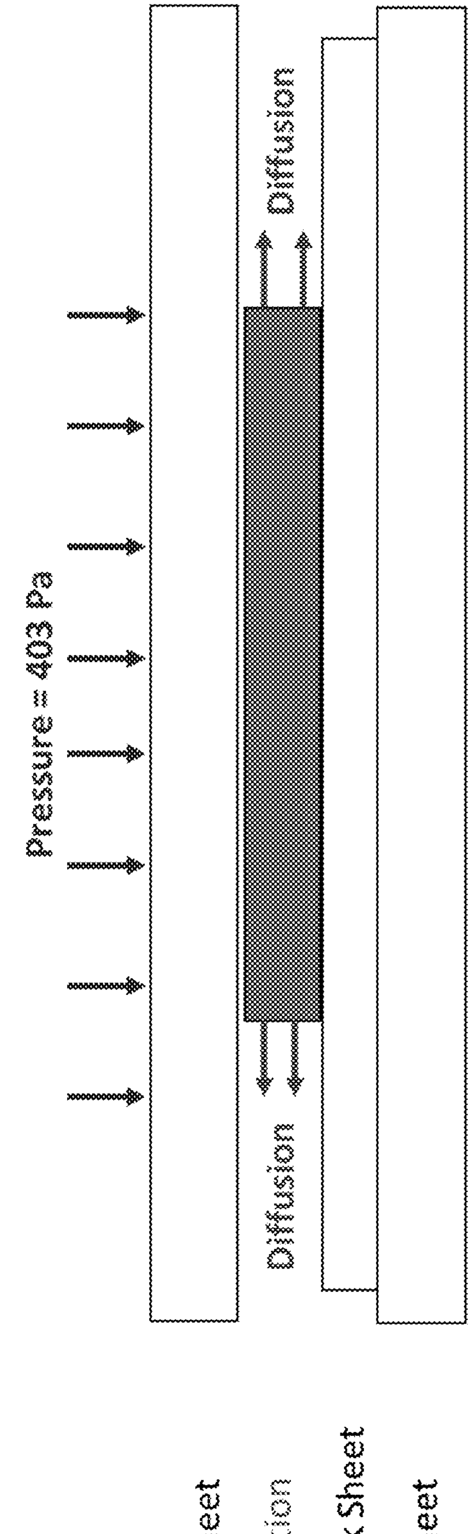
FIG. 20 provides an example fixture for placing a CNF coating onto cardstock.

FIG. 20 provides an example fixture for placing a CNF coating onto cardstock.

Figure 21:
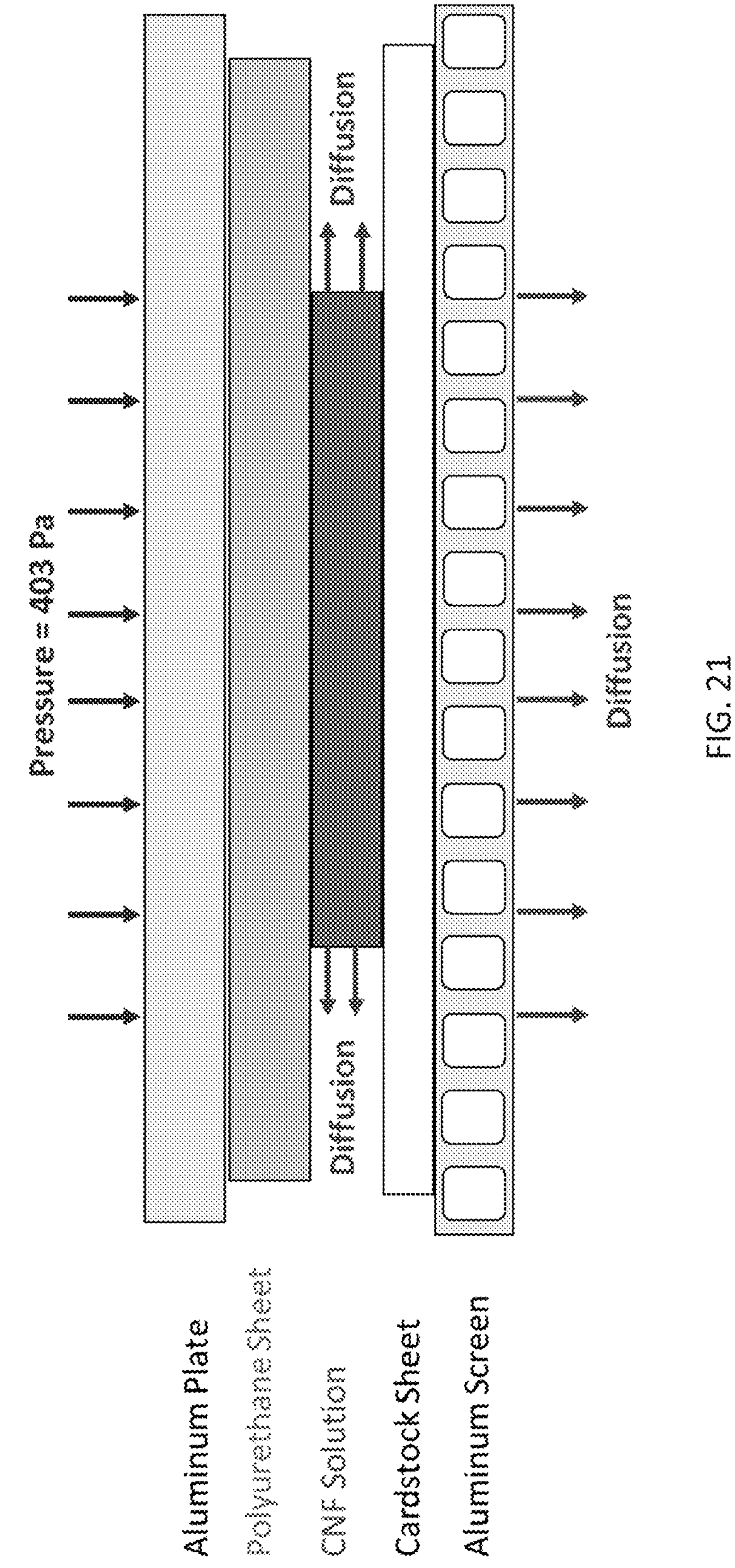
FIG. 21 provides an example fixture for placing a CNF coating onto cardstock.

FIG. 21 provides an example fixture for placing a CNF coating onto cardstock. As shown, pressure (the 403 Pa pressure shown in FIG. 21 is exemplary only and does not limit the scope of the present disclosure or the appended claims) can be applied with an aluminum, metal, or other rigid material plate. A spacer sheet—which can be an elastomer, such as polyurethane—can be placed between the plate and the CNF solution that is placed atop the cardstock or other scaffold material. The spacer sheet can be resilient; for example, a rubber can be used in the spacer sheet. As shown, a screen—which screen can be, for example, an aluminum or other metal screen—can be placed below the substrate.

Figure 22:
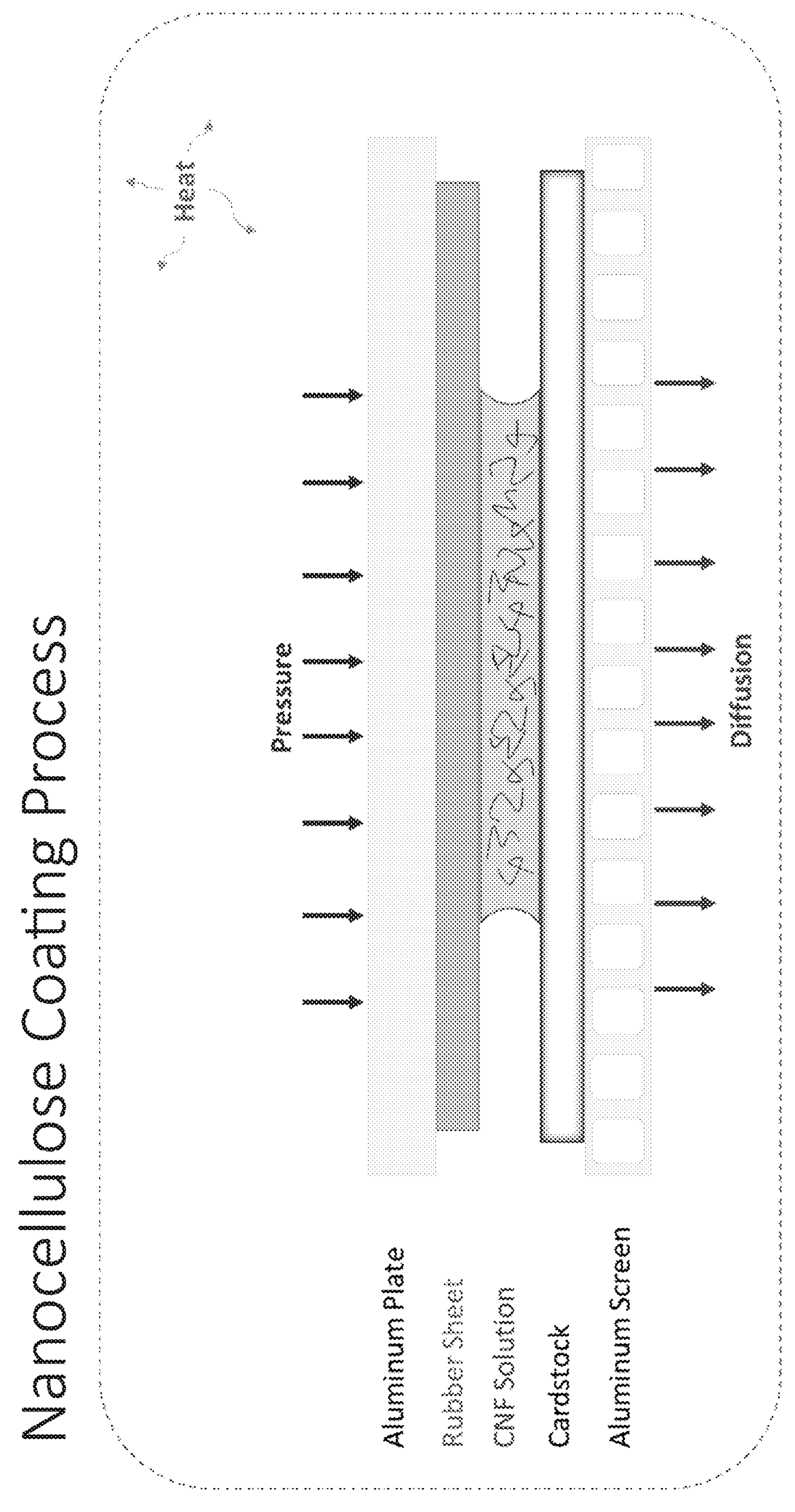
FIG. 22 provides an example process for placing a CNF coating onto cardstock.

Without being bound to any particular theory or embodiment, excess moisture can be communicated out of the holes of the screen. As shown, the presence of the porous aluminum screen can operate to enhance diffusion of the CNF solution during processing, and the presence of the spacer sheet above the CNF solution can act to decrease adhesion. Without being bound to any particular theory or embodiment, the spacer sheet can be selected to be a material to which the CNF does not adhere well to compared to the adhesion between the CNF and the scaffold that is being coated. As shown in FIG. 22, one can apply heat during performance of some or all of the method; without being bound to any particular theory or embodiment, the presence of heat can encourage drying of the applied CNF solution.

Without being bound to any particular theory or embodiment, the rubber sheet can act to reduce or even eliminate warping of the rigid plate. Further, because CNF may prefer to bond to cardstock or another substrate over bonding to the rubber sheet, the presence of the rubber sheet can prevent sticking by the CNF during the coating process.

Without being bound to any particular theory or embodiment, the use of a fixture according to FIG. 21 can result in improved surface smoothness of the coated substrate as well as improved coverage by the CNF solution as compared to samples made with a fixture according to FIG. 20.

FIG. 22 provides an example process for placing a CNF coating onto cardstock.

FIG. 23 provides a comparison of results obtained with a fixture according to FIG. 20 ("Old Acrylic Fixture") and with a fixture according to FIG. 21 ("New Aluminum Fixture").

FIG. 24 provides an exemplary screen printing process. As shown, pressure can be applied via a squeegee to a paste that is applied to a screen, leaving behind a patterned print deposit as shown on a substrate.

FIG. 25 provides exemplary features made on a cardstock substrate, a nano cellulose infiltrated paper (NCIP) substrate, and a polyimide substrate. As seen, the features printed on NCIP and polyimide exhibit greater fidelity than the features printed on cardstock. Thus, the disclosed technology can be used to form features printed on NCIP that more closely match the nominally prescribed manufacturing dimensions than of those features printed on cardstock.

Additional Disclosure

Flexible and printed electronics have garnered significant research and commercial interest over the last several decades.[1,2] This has been in large part due to the rapid growth of applications in fields such as personal health monitoring, robotically assisted medical and surgical procedures, and agricultural monitoring. With the increased use of Internet of Things (IoT) solutions in such applications, the need for increased data collection through high sensor density is becoming more prevalent. Traditional MEMS based devices[3-5] are not well suited for such uses due to their high unit cost. Consequently, lower cost printed electronics have shown to be a promising alternative for IoT applications.

Traditional flexible electronics are developed on engineered polymer substrates, such as polyimide (PI), polyethylene napthalate (PEN), and polyethylene terephtalate (PET). These materials are chosen due to their surface smoothness, thermal stability, favorable barrier properties (diffusion and gas permeability), mechanical robustness and low manufacturing cost.[2,6] However, sustainability is a major concern with these and other synthetic polymer substrates that are non-biodegradable.[7] In applications like precision agriculture and smart packaging, e-waste from such engineered polymer substrates limits the wide adoption of printed electronics. There is a critical need for sustainable, renewable, and biodegradable material alternatives for flexible electronics.

Cellulose, the most abundant natural polymer on earth, has been widely explored as a candidate substrate for use in flexible and printed electronics due to it being non-toxic, biodegradable, and in ample supply.[8] Of the many different types of cellulose-based materials, pulp-based micro cellulose paper has been studied the most as an electronic substrate material.[9-13] One of the benefits of using paper substrates, such as cardstock, is that they are compliant and have the mechanical robustness necessary for flexible electronics applications. Specifically, the hygroscopic property of cellulose based materials makes them attractive options for humidity and soil moisture sensing.[14] When exposed to moisture, void spaces within the fiber network become filled with water. Since the dielectric constant of water is larger than that of air ($\in H_2O=78.4$, $\in_{air}=1$), this results in an overall increase in the dielectric constant. The change in dielectric constant can be measured using screen printed capacitive sensors which respond to monitor moisture change in the cellulose-based substrate.

Though cellulose based substrates have desirable properties like biodegradability and moisture sorption, the printed structures on these substrates exhibit inferior electrical performance compared to those on engineered polymer materials. This can be attributed to the surface roughness and high porosity of the substrate, as printed structures lack geometric consistency with decreasing smoothness. A common method to improve the unfavorable surface and barrier properties of cellulose substrates is to coat them with polymer fillers. While such devices exhibit improved performance, these cellulose substrates are not biodegradable or cost effective.[15,16]

In search of alternate solutions, recent research has turned to substrates made from nanocellulose, specifically cellulose nanofibers (CNF). When formed into films, CNFs exhibit exceptional specific stiffness and strength.[17] The small size of the constituent fibers and their high aspect ratio allow them to form into tight networks that result in a high degree of surface smoothness. Due to chemical functionalization, nanocellulose has surface hydroxyl and carboxyl groups that are available for water molecules to adsorb to. This increases the polarizability of the group and also increases the dielectric constant of the material.[18,19] Various works have leveraged this property to develop humidity sensors on neat CNF films that have demonstrated a wide sensing range and high sensitivity.[20-22]

Though these studies have shown working sensors, the limited mechanical stability of pure nanocellulose films when cycled under varying moisture conditions makes them unsuitable for many applications.[23] Pure CNF films, while possessing exceptional specific stiffness, are known to be brittle and require the addition of plasticizers[24] to endow them with ductility. While these composite films are mechanically suitable, they are not economically viable for large scale manufacturing and implementation. Therefore, there is a need to develop inexpensive biodegradable materials that can realize the benefits of nanocellulose.

In this disclosure, we present a nano cellulose infiltrated paper (NCIP) consisting of cardstock coated with a surface layer of CNF. The surface coating of CNF achieves a low surface roughness using only a fraction of the material used for neat CNF films of the same size. We also provide a fabrication method for making these materials and characterize the surface properties of the NCIP. We then present fabricating printed electronic structures on the substrate by assessing the geometric and electrical quality of screen printed capacitors.

The moisture response and electrical properties of the NCIP are characterized and highlight its suitability both as a substrate and as a responsive material for moisture sensing. Moisture transport into the NCIP is measured to ensure material response time is fast enough for applications in the agricultural, medical, and packaging industries.

Materials and Methods

NCIP Fabrication

Nanocellulose Infiltrated Paper (NCIP) samples were fabricated via infiltration of a CNF solution into 8.5"×11" cardstock paper (Neenah) with an approximate thickness of 200 μm. The CNF solution is prepared from a 1.47 mmol COONa/g dry CNF in sodium form that has been mixed with water to create a 0.99 wt % TEMPO-oxidized CNF gel (obtained from USDA Forest Products Laboratory). To prepare the coating solution, the CNF gel is combined with deionized water in a 1:1 ratio to form a 0.5 wt % mixture. This mixture is then magnetically stirred at 500 RPM for 10 minutes to uniformly mix the CNF with the deionized water and prepare a homogeneous solution. The solution is then centrifuged at 3000 RPM for 3 minutes to ensure that cellulose nanofibril strands do not agglomerate and are uniformly dispersed. The solution is then stored at 7° C. for at least 12 hours to ensure uniform viscosity of the solution.

A schematic of the fabrication process is given in FIG. 11. To prepare the NCIP, two ¼", 9"×12" laser cut PMMA pieces are used. A sheet of letter sized cardstock is uniformly wet and pressed against one of the PMMA sheets. The paper is wet to allow the porous structure of the cardstock to expand so that the CNF solution can infiltrate into the surface. Wetting the paper also minimizes drying deformations that might occur since having a sheet that is uniformly wet will encourage a uniform drying gradient. 18 grams of CNF solution are deposited into the center of the wet cardstock and the second piece of PMMA is brought down parallel to the surface of the cardstock and pressed to evenly distribute the CNF solution into a thin and continuous layer ($0.035\ m^2$). Depositing the CNF in the center in one mound is key as without this step, air bubbles are very likely to form during the pressing step, leading to a non-uniform layer. After pressing the second piece into contact, a known mass of 2.5 kg is used to apply a nominal pressure of 406 Pa. This value was found to ensure a uniform distribution of the CNF solution. The assembly was then dried in the oven at 60° C. for 15 hours to remove excess moisture and form the surface film. A secondary drying step at 45 C for 1 hour was performed with the coated paper removed from the fixture to ensure dryness.

Substrate Surface Characterization

Scanning electron microscopy (SEM, FEI Quanta 600) was used to image the surface of the NCIP and cardstock substrates to understand the impact of coating on surface topography. In addition, the cross section of a NCIP sample was captured using SEM to identify the nominal thickness of the CNF layer. For the cross section imaging, samples were prepared by embedding NCIP specimens into Epo-Fix resin. The resin was allowed to cure and a Reichert Ultracut S microtome was used to expose the cross section.

The surface roughness of each substrate was measured using White Light Interferometry (WLI, Zygo New View 6300 Interferometer). Measurements were conducted using a 10× objective over an area of $0.37\ mm^2$. To improve the quality of the WLI data, substrates were sputter coated with a 10 nm layer of iridium prior to measurement to ensure uniformity in the reflectivity of the substrate. To quantify surface roughness variations within and across samples, 5 different samples were measured per substrate, with each sample measured at five locations (center, and the four corners) for a total of 25 data sets.

Screen-Printed Structures

To assess the quality of printed structures on the NCIP, capacitive structures were fabricated on the NCIP, cardstock, and polyimide via screen printing. In all printing trials here, a MSP-485 semi-automatic screen printer from HMI (Hary Manufacturing Inc) was used with a 80 shore hardness squeegee blade and a high viscosity silver nanoflake ink (HPS-FG77, NovaCentrix). Two different interdigitated capacitors were printed and evaluated (0.5 pF and 1 pF), with all samples annealed at 150° C. for 1 hour after printing. The small and large capacitive structures consisted of 10 fingers both with trace widths and spacings of 100 μm and 250 μm and lengths of 3.1 mm and 7.5 mm respectively. The goal was to evaluate the effect of feature size (finger length) on print quality. Optical microscope images of the capacitors can be found in the supplementary information.

Assessment of Screen Printed Structures

To assess if the reduction in surface roughness translated to an improvement in the quality of the printed structures, optical microscopy and image analysis were used to quantify feature dimensions. All images were taken using an Axio Imager. A1m microscope (Carl Zeiss AG) with a 10× objective. Five different printed structures were imaged for each capacitor design and substrate combination. For each sample, five different 1 mm long interdigitated fingers were imaged to capture any spatial variation. Image processing was then conducted to extract average trace width and Line Edge Roughness (LER) for each sample.

LER is a common metric used to characterize photolithographically fabricated devices.[25] LER is a roughness parameter that measures the deviation of a feature from a prescribed value. Here, we define LER as the RMS roughness of the trace edge from a vertically straight line. Additional details about the image processing, roughness calculations as well as width and spacing measurements for each sample can be found in the supplementary information.

To evaluate the correlation between LER/surface roughness and electrical performance of the printed structures, the capacitance and phase angle of all capacitor samples were measured using an LCR meter at 8 MHz. This measurement was taken at a relative humidity of 40% RH and a temperature of 22.6° C. The variance and error with respect to designed capacitance were quantified for each substrate of polyimide, cardstock, and NCIP.

Moisture Response Characterization

The moisture content change and substrate sorption time was measured by collecting moisture uptake data using a precision balance (Mettler Toledo XSR205) enclosed in a chamber with controlled humidity. Data was collected for NCIP samples and plain cardstock. Samples for both materials were first cut into 0.75"×0.75" squares. This size was chosen as it is the nominal footprint of the capacitive structures used in this work. Samples were dried overnight under vacuum at 110° C. to remove all moisture from the substrates and the 0% moisture mass was recorded. Data was collected for three different humidity conditions, 30%, 50%, and 70% to capture the behavior of the NCIP over a range of relative humidities. Mass data was recorded at 30 second intervals for 2 hours, with three samples tested per substrate at each humidity condition.

Hysteresis is an important consideration for paper, as the amount of moisture taken up by the cellulose can vary with cycling. For moisture cycling experiments, 0.75"×0.75" square NCIP samples were prepared and stored in a sealed environment with 55% RH two-way humidity packs (Boveda Inc.) to saturate for 24 hours, mimicking a sensor pre-conditioning step. As before, samples were placed on the precision balance and the humidity chamber was sealed.

For this test, the humidity was set to 85% RH, representing a Δ30% RH with respect to the storage condition, and mass data was recorded at 30 second intervals for 2 hours. Samples were then moved back into the 55% RH sealed environment for a few minutes while the chamber equilibrated to the lower set point of 55% RH before being moved back and resuming data collection for another two hours. This process was repeated for another full 4 hour cycle and conducted on a total of 3 NCIP samples. The moisture uptake behavior of the NCIP was moedlled using the Parallel Exponential Kinetics (PEK) model, which has been shown to accurately describe the moisture response of cellulose nanofiber films.[26-28].

The capacitive moisture sensors screen printed on the NCIP substrate were used to evaluate the humidity response time of the printed structure. The large moisture sensors printed on NCIP were hooked up to a potentiostat (Palmsens EmStat4s) and placed in the humidity chamber. The impedance was measured at a frequency of 17 kHz and 20 kHz with an input DC voltage of 2V and oscillating voltage of 0.25V. Impedance was measured every 10 seconds while humidity was varied from 20-50% RH in increments of 10% RH for intervals of 1 hour. Response time was extracted from collected data and compared to moisture uptake data collected using the precision balance.

Results and Discussion

Surface Properties

Micro cellulose fibers which comprise pulp-based papers have high surface roughness and porosity. As a result, printed structures suffer from issues of ink infiltration, feature edge roughness and adhesion, which together result in unrepeatable and low-quality structures with inadequate electrical properties.[29,30] Here, we assess the improvement in surface quality and in the quality of printed structures that is realized through a surface coating of CNF.

As can be seen from FIG. 13A, the surface of cardstock is composed of an entangled network of microscale cellulose fibers, as is typical of pulp-based papers. The fibers overlap with each other, creating a rough surface with a high porosity. When the cardstock is coated with a layer of CNF solution, it infiltrates into the surface pores and forms a uniform layer (FIG. 13B). This is due to the fact that cellulose nano fibers can bind together well to create a tight network. From the cross-sectional image (FIG. 13C), it can be seen that the CNF is bound to the surface of the cardstock in a highly densified and distinct layer. We find that the thickness of the layer is 5 μm-7 μm in thickness, with variations due to any inconsistencies in the fabrication process.

To quantify this improvement, average $R_q$ values and standard deviations for each substrate were calculated and plotted in Table 1. Cardstock exhibited the largest surface roughness with an $R_q$ of 4.3±0.31 μm, while the NCIP had a much lower $R_q$ of 189±42 nm. This is consistent with what was observed in the surface SEM imaging in FIG. 13C, where the visible fiber entanglement and porosity of the cardstock results in a highly rough surface. By coating with the CNF layer, planarization of the surface is achieved, resulting in an order of magnitude reduction in the $R_q$. It should be noted, however, that the polyimide was the smoothest substrate, with an $R_q$ of 45±21 nm. Dish dried CNF films with $R_q$ values of 4 nm have been reported,[31] indicating that it is possible to achieve smoother films with further refinement of the fabrication process. Substrate roughness is an important parameter as it affects the resolution of the printed features.

TABLE 1

| Substrate Surface Roughness<br>Substrate |
|---|
| Cardstock: 4.3 ± 0.31 μm |
| NCIP: 189 ± 42 nm |
| Polyimide: 45 ± 21 nm |

Quality of Screen Printed Structures

The average trace width for each capacitor size/substrate combination was calculated and plotted in FIG. 14A. It can be seen that there is no difference in the average trace width values across polyimide, NCIP, and cardstock. This can be attributed to the fact that an average value is computed here. There are equal amounts of the trace that are thinner and thicker than the nominal width by the same amount such that they offset each other and result in average values similar to the those for the NCIP and polyimide.

Line Edge Roughness (LER) was calculated to assess trace quality. The calculated LER values for each substrate/capacitor size combination are plotted in FIG. 14C. For both capacitor sizes, traces printed on cardstock exhibited a 1.7× larger LER than for those printed on polyimide and NCIP, which is consistent with what is observed in the images. The capacitance scales non-linearly with electrode spacing, meaning that a large LER indicates greater variations in the gap and therefore the capacitance. The equation for a capacitor is given by:

$$C = \frac{\epsilon_r \epsilon_0 A}{g} \quad (1)$$

Where A is the overlap area of the fingers, $\in_r$ is the relative permittivity of the material and $\in_o$ is the permittivity of free space $$\left(8.854 \times 10^{-12} \frac{F}{m}\right)$$

and g is the spacing between the traces. This is undesirable as batch to batch consistency in device properties is crucial for manufacturing scalability.

To understand the effect of LER and surface roughness on electrical properties, the capacitance and phase angle values were measured for 5 printed structures. The average value and standard deviation were calculated and plotted (FIG. 15A-15D). While the capacitance of structures screen printed on polyimide and NCIP substrates have low standard deviation and an average value close to the estimated capacitance of the designed structure, those printed on cardstock exhibited deviations from nominal values and substantial standard deviations, reflecting significant device-to-device variation.

From these capacitance measurements it can be seen that LER and surface roughness can be correlated with expected sensor performance. The CNF coating provides surface smoothness for a paper substrate that is comparable to polyimide. The phase angle of all substrates is relatively close to −90°, indicating that all substrates are suitable for capacitive sensing.

Moisture Response

The NCIP substrates were evaluated for use in moisture sensing. Important aspects of moisture sensing are response time and repeatability. FIGS. 16A-16B show the average moisture uptake curves for cardstock and NCIP along with the PEK model fit to the data. The PEK model consists of two processes, a fast process and a slow process. The model fit parameters for cardstock and NCIP are given in Table 2 and Table 3 respectively. The subscripts 1 and 2 denote the parameters for the fast and slow processes, respectively.

A few important observations can be made from the extracted parameters. While the total equilibrium moisture content (EMC) ($MC_1$+$MC_2$) for the cardstock and NCIP samples are similar across the three humidity conditions, the cardstock samples saturate much quicker than the NCIP samples. This can be seen from the values of $\tau_1$, which are consistently lower for all humidity conditions, caused by the large fiber and pore size in the cardstock vs. the CNF layer. The cardstock is composed of microcellulose fibrils, which are several orders of magnitude larger than CNFs. Because of this, the total available fiber surface area and the space between fibers is much greater, allowing for water to be more easily taken up. This can be qualitatively seen in the surface SEM image of the cardstock in FIG. 13A where the interfibril pore space is clearly visible and from the values of $MC_1$ being greater than $MC_2$, indicating that the majority of water sorption is occuring due to the large pore spacing. Note that this does not translate to a greater total EMC compared to the NCIP. This is likely due to the TEMPO-mediated oxidation of the CNFs that were used. TEMPO oxidation results in a high density of hydrophilic carboxyl groups on the surface of the CNFs, creating additional bonding sites for water molecules.[32] This increased density seems to offset the lower available surface area, resulting in similar EMCs across all tested RH conditions.

While the EMC and sorption timescales are highly dependent on the specific type of nanocellulose used and on the processing conditions, the MC and τ values obtained agree well with PEK parameters reported for CNF in the literature.[26-28] This is because the ability of cellulose to absorb and adsorb water to open sites is determined by its degree and amount of crystallinity.[33,34]

Although there is no consensus on the exact physical mechanisms,[35,36] both processes are attributed to the resistance of the cellulose matrix to deformation due to the uptake of moisture at the surface. It has been posited that the fast process corresponds to the swelling of the cellulose matrix as moisture is initially adsorbed and volume change occurs, while the slow process is due to additional water being sorbed as the cellulose network relaxes and new sorption points become available.[35,37,38]

TABLE 2

Parallel Exponential Kinetic (PEK) Model Parameters (Cardstock)

| | 30% | 50% | 70% |
|---|---|---|---|
| $MC_1$ (%) | 2.22 | 4.14 | 4.48 |
| $MC_2$ (%) | 0.75 | 0.59 | 2.98 |
| $\tau_1$ (min) | 6.8 | 4.23 | 2.84 |
| $\tau_2$ (min) | 22 | 15 | 11.45 |

TABLE 3

Parallel Exponential Kinetic (PEK) Model Parameters (NCIP)

| | 30% | 50% | 70% |
|---|---|---|---|
| $MC_1$ (%) | 0.32 | 1.94 | 5.25 |
| $MC_2$ (%) | 3.04 | 3.21 | 1.29 |
| $\tau_1$ (min) | 4.75 | 11.1 | 6.43 |
| $\tau_2$ (min) | 22.22 | 11.15 | 24.93 |

In a real-world scenario, sensors will experience both moisture uptake and release over several cycles. This can affect the EMC and time constants due to hysteretic effects. To investigate how this affects the moisture response, humidity cycling tests were performed on the NCIP. FIGS. 17A-17B show the average moisture cycling data for the NCIP along with the PEK model fit for both up ramp and down ramp cycles. The model fit parameters for the cycling data are given in Table 4.

TABLE 4

Parallel Exponential Model Parameters for ΔRH = 30% (NCIP)

| | Dry | Up Ramp 1 | Up Ramp 2 | Down Ramp 1 | Down Ramp 2 |
|---|---|---|---|---|---|
| $MC_1$ (%) | 0.32 | 4.141 | 1.432 | 20.12 | 1.96 |
| $MC_2$ (%) | 3.04 | 0.724 | 3.486 | 0.742 | 0.85 |

TABLE 4-continued

| Parallel Exponential Model Parameters for ΔRH = 30% (NCIP) | | | | | |
|---|---|---|---|---|---|
| | Dry | Up Ramp 1 | Up Ramp 2 | Down Ramp 1 | Down Ramp 2 |
| $\tau_1$ (min) | 4.75 | 7.51 | 12 | 4.59 | 3.66 |
| $\tau_2$ (min) | 22.22 | 60 | 1.66 | 20.93 | 23.27 |

The EMC of the cycling data at 55% RH is lower than the EMC for the dried samples (FIG. 13B). This can be attributed to the humidity packs used during the saturation step for the cycled samples. The humidity packs achieve the desired humidity set point using a salt solution. As the packs release moisture, they also release the salt ions, which accumulate on the substrate surface, occupying sites that water molecules would otherwise fill. This leads to the total possible moisture content of the sample being smaller than in the case of exposure to water vapor.[39]

In examining the moisture response of the first and second up ramp cycles, it can be seen that there is hysteresis between the two cycles with saturation occurring much faster during the second ramp than the first. When the CNF layer is initially exposed to the high humidity environment, it uptakes moisture, causing swelling of the matrix and the collapse of nano pores. This hinders moisture uptake, causing a delay in the saturation response.[27,40] During the second cycle, the nano pores have not had a chance to reform and so there is no delay in the moisture uptake behavior. This is reflected in the $\tau$ values, where the first up ramp has a large $\tau_2$ value associated with the gradual collapse of the nano pores, whereas both time constants for the second up ramp are short. Conversely, the down ramp behavior for both cycles are nearly identical, with both the shape of the moisture curve and the associated time constants matching. This can be attributed to the fact that during the down ramp, the ambient environment is the reservoir into which moisture is being released. The large volume of the testing environment relative to the volume of the sample means there is nothing impeding the desorption of water in either cycle.

The saturation moisture contents at both low and high humidity are the same between cycles, indicating that the amount of trapped water in the cellulose is very small. This is favorable as it demonstrates repeatability in the steady state moisture response of the material during cycling.

Dielectric Change Leveraged in Moisture Sensing

The response time of the capacitive moisture sensors was measured and compared to the moisture uptake time of the substrate. Figure . . . shows the humidity varied between 20-50% RH in increments of 10% RH while impedance, capacitance, and phase angle was collected. The response time for each increment was measured and tabulated. It can be seen that the moisture uptake response of the substrate is on the same order as the capacitive response time of the sensor. This indicates that the capacitance of sensors fabricated on the NCIP respond in tandem with changes in the moisture content. For applications such as soil moisture sensing and humidity sensing these response times are acceptable.

Additional Results

Table 5 below provides exemplary data comparing samples obtained using a fixture according to FIG. 20 and a fixture according to FIG. 21, by references to the measurement approach shown in FIG. 26.

TABLE 5

| | | | Acrylic Fixture | | | Aluminum Fixture | | |
|---|---|---|---|---|---|---|---|---|
| Description | Variable | Unit | A1 | A2 | A3 | B1 | B2 | B3 |
| Ellipse Diameter a | d_a | [cm] | 13 | 15 | 17 | 25 | 21 | 21 |
| Ellipse Diameter b | d_b | [cm] | 16 | 19 | 17 | 13 | 20 | 20 |
| Coated Area (pi*d_a*d_b) | A | [cm^2] | 163 | 224 | 227 | 255 | 330 | 330 |
| Out of Plane Deformation | z | [cm] | 1.75 | 2.50 | 2.00 | 0.25 | 0.40 | 0.75 |

As shown above, the use of an aluminum fixture according to FIG. 21 resulted in improved performance as compared to the use of an acrylic fixture according to FIG. 20. First, the ellipse formed by pressing on an amount of CNF solution was of a greater area when using a fixture according to FIG. 21. Further, the out of plane deformation was reduced when using a fixture according to FIG. 21 as compared to a fixture according to FIG. 20.

Table 6 below provides additional data comparing samples obtained using a fixture according to FIG. 20 and a fixture according to FIG. 21, by references to the measurement approach shown in FIG. 26.

TABLE 5

| Description | Unit | Acrylic Fixture | Aluminum Fixture |
|---|---|---|---|
| Coated Area (pi*d_a*d_b) | [cm^2] | 205 | 305 |
| Out of Plane Deformation | [cm] | 2.08 | 0.47 |
| Number of Fixture Uses | [—] | ~7 | Unlimited |
| Drying Time at 60 C. | [hr] | 15 | 4 |
| Drying Time of Second Drying Step | [hr] | 1 | N/A |

As shown above, the use of an aluminum fixture according to FIG. 21 resulted in improved performance as compared to the use of an acrylic fixture according to FIG. 20. First, the coated area formed by pressing on an amount of CNF solution was of a greater area when using a fixture according to FIG. 21. Second, the out of plane deformation was reduced when using a fixture according to FIG. 21 as compared to a fixture according to FIG. 20. Further, the aluminum fixture was shown to be more durable than the acrylic fixture, as the acrylic fixture was useful for only a few cycles. Further, the drying time was improved when using an aluminum fixture according to FIG. 21.

CONCLUSION

A fully-biodegradable paper-based substrate was presented for use in printed electronics applications. To improve the surface properties of paper substrates, a cellulose nanofibril coating was applied showing surface roughness values comparable to widely-used polyimide substrates. To exploit the benefits of nanocellulose, a fabrication process for making a nanocellulose infiltrated paper (NCIP) was presented. The surface properties of the NCIP were characterized through optical and SEM imaging and it was found that the surface coating of CNF reduced the surface roughness of cardstock by an order of magnitude and resulted in $R_q$ values similar to that of polyimide. This was reflected in the electrical properties of the printed structures, with capacitors fabricated on the NCIP exhibiting consistent capacitance and phase angles similar to structures on polyimide. The fabrication of silver-ink structures through screen printing resulted in capacitive sensors with less geometric variability and more consistent electrical measurements.

These substrates are ideal for moisture related sensing due to the hygroscopic nature of cellulose as seen in the literature. To evaluate the impact of the nanocellulose coating on the substrate transport properties, the moisture uptake time and hysteresis were quantified. The moisture response of the NCIP was experimentally measured under various humidity conditions and modelled using the Parallel Exponential Kinetics (PEK) model. The moisture response was found to be consistent across multiple humidity ramp cycles, and the extracted time constants were consistent with those observed in our previous work. It was shown that the NCIP substrate reaches 95% of its moisture mass as compared to cardstock substrates. After cycling experiments, hysteresis leads to a change in water uptake. The capacitive moisture sensors designed in previous work[41] were fabricated on the NCIP substrate. These moisture uptake measurements show how the material properties of cellulose can be leveraged for active sensing.

Pulp-based papers, while biodegradable, are unsuitable for flexible and printed electronics applications due to their poor surface properties. While pure nanocellulose films are promising alternatives, they are expensive and lack the mechanical stability necessary for such applications. Due to the hygroscopic nature of CNFs, the NCIP can be used for developing moisture sensors. From the characterization of surface, mechanical, and moisture transport properties, NCIP substrates are fully biodegradable substrates with better electrical performance than pure pulp-based papers and have the added benefit of active material properties that engineered polymer substrates do not possess.

REFERENCES (1) Tong, G.; Jia, Z.; Chang, J. Flexible Hybrid Electronics: Review and Challenges, 2018 IEEE International Symposium on Circuits and Systems (ISCAS). Florence, 2018; pp 1-5.

(2) Khan, Y.; Thielens, A.; Muin, S.; Ting, J.; Baumbauer, C.; Arias, A. C. A New Frontier of Printed Electronics: Flexible Hybrid Electronics. *Advanced Materials* 2020, 32, 1905279.

(3) Wang, Z.; Sun, L.; Ni, Y.; Liu, L.; Xu, W. Flexible Electronics and Healthcare Applications. *Frontiers in Nanotechnology* 2021, 3, 625989.

(4) Heng, W.; Solomon, S.; Gao, W. Flexible Electronics and Devices as Human-Machine Interfaces for Medical Robotics. *Advanced Materials* 2022, 34, 2107902.

(5) Wang, X.; Liu, Z.; Zhang, T. Flexible Sensing Electronics for Wearable/Attachable Health Monitoring. *Small* 2017, 13, 1602790.

(6) MacDonald, W. A.; Looney, M. K.; MacKerron, D.; Eveson, R.; Adam, R.; Hashimoto, K.; Rakos, K. Latest advances in substrates for flexible electronics. *Journal of the Society for Information Display* 2007, 15, 1075.

(7) Garcia, J. M.; Robertson, M. L. The future of plastics recycling. *Science* 2017, 358, 870-872.

(8) Rajinipriya, M.; Nagalakshmaiah, M.; Robert, M.; Elkoun, S. Importance of Agricultural and Industrial Waste in the Field of Nanocellulose and Recent Industrial Developments of Wood Based Nanocellulose: A Review. *ACS Sustainable Chemistry & Engineering* 2018, 6, 2807-2828.

(9) Yang, L.; Rida, A.; Vyas, R.; Tentzeris, M. M. RFID Tag and RF Structures on a Paper Substrate Using Inkjet-Printing Technology. *IEEE Transactions on Microwave Theory and Techniques* 2007, 55, 2894-2901.

(10) Wang, Y.; Yan, C.; Cheng, S.; Xu, Z.; Sun, X.; Xu, Y.; Chen, J.; Jiang, Z.; Liang, K.; Feng, Z. Flexible RFID Tag Metal Antenna on Paper-Based Substrate by Inkjet Printing Technology. *Advanced Functional Materials* 2019, 29, 1902579.

(11) Kim, S.; Cook, B.; Le, T.; Cooper, J.; Lee, H.; Lakafosis, V.; Vyas, R.; Moro, R.; Bozzi, M.; Georgiadis, A.; Collado, A.; Tentzeris, M. M. Inkjet-printed antennas, sensors and circuits on paper substrate. *IET Microwaves, Antennas & Propagation* 2013, 7, 858-868.

(12) Shaker, G.; Safavi-Naeini, S.; Sangary, N.; Tentzeris, M. M. Inkjet Printing of Ultrawideband (UWB) Antennas on Paper-Based Substrates. *IEEE Antennas and Wireless Propagation Letters* 2011, 10, 111-114.

(13) Li, X.; Sidén, J.; Andersson, H.; Schön, T. A Paper-Based Screen Printed HF RFID Reader Antenna System. *IEEE Journal of Radio Frequency Identification* 2018, 2, 118-126.

(14) Kim, S.; Le, T.; Tentzeris, M. M.; Harrabi, A.; Collado, A.; Georgiadis, A. An RFIDenabled inkjet-printed soil moisture sensor on paper for “smart” agricultural applications. IEEE SENSORS 2014 Proceedings. Valencia, Spain, 2014; pp 1507-1510.

(15) Ihalainen, P.; Määttänen, A.; Järnström, J.; Tobjörk, D.; Österbacka, R.; Peltonen, J. Influence of Surface Properties of Coated Papers on Printed Electronics. *Industrial & Engineering Chemistry Research* 2012, 51, 6025-6036.

(16) Larsson, M.; Engström, G.; Vidal, D.; Zou, X. Compression of Coating Structures During Calendering. 20.

(17) Isogai, A.; Saito, T.; Fukuzumi, H. TEMPO-oxidized cellulose nanofibers. *Nanoscale* 2011, 3, 71-85.

(18) Le Bras, D.; Strømme, M.; Mihranyan, A. Characterization of Dielectric Properties of Nanocellulose from Wood and Algae for Electrical Insulator Applications. *The Journal of Physical Chemistry B* 2015, 119, 5911-5917.

(19) Luo, Q.; Shen, H.; Zhou, G.; Xu, X. A mini-review on the dielectric properties of cellulose and nanocellulose-based materials as electronic components. *Carbohydrate Polymers* 2023, 303, 120449.

(20) Rivadeneyra, A.; Marín-Sánchez, A.; Wicklein, B.; Salmerón, J. F.; Castillo, E.; Bobinger, M.; Salinas-Castillo, A. Cellulose nanofibers as substrate for flexible and biodegradable moisture sensors. *Composites Science and Technology* 2021, 208, 108738.

(21) Ayissi Eyebe, G.; Bideau, B.; Boubekeur, N.; Loranger; Domingue, F. Environmentally-friendly cellulose nanofibre sheets for humidity sensing in microwave frequencies. *Sensors and Actuators B: Chemical* 2017, 245, 484-492.

(22) Syrový, T.; Maronová, S.; Kuberský, P.; Ehman, N. V.; Vallejos, M. E.; Pretl, S.; Felissia, F. E.; Area, M. C.; Chinga-Carrasco, G. Wide range humidity sensors printed on biocomposite films of cellulose nanofibril and poly (ethylene glycol). *Journal of Applied Polymer Science* 2019, 136, 47920.

(23) Hasan, I.; Wang, J.; Tajvidi, M. Tuning physical, mechanical and barrier properties of cellulose nanofibril films through film drying techniques coupled with thermal compression. *Cellulose* 2021, 28, 11345-11366.

(24) Jaiswal, A. K.; Kumar, V.; Jansson, E.; Huttunen, O.; Yamamoto, A.; Vikman, M.; Khakalo, A.; Hiltunen, J.; Behfar, M. H. Biodegradable Cellulose Nanocomposite Substrate for Recyclable Flexible Printed Electronics. *Advanced Electronic Materials* 2023, 2201094.

(25) Croon, J.; Storms, G.; Winkelmeier, S.; Pollentier, I.; Ercken, M.; Decoutere, S.; Sansen, W.; Maes, H. Line edge roughness: characterization, modeling and impact on device behavior. Digest. International Electron Devices Meeting, San Francisco, CA, USA, 2002; pp 307-310.

(26) Lundahl, M. J.; Cunha, A. G.; Rojo, E.; Papageorgiou, A. C.; Rautkari, L.; Arboleda, J. C.; Rojas, O. J. Strength and Water Interactions of Cellulose I Filaments Wet-Spun from Cellulose Nanofibril Hydrogels. *Scientific Reports* 2016, 6, 30695.

(27) Guo, X.; Wu, Y.; Xie, X. Water vapor sorption properties of cellulose nanocrystals and nanofibers using dynamic vapor sorption apparatus. *Scientific Reports* 2017, 7, 14207.

(28) Torstensen, J.; Liu, M.; Jin, S.-A.; Deng, L.; Hawari, A. I.; Syverud, K.; Spontak, R. J.; Gregersen, W. Swelling and Free-Volume Characteristics of TEMPO-Oxidized Cellulose Nanofibril Films. *Biomacromolecules* 2018, 19, 1016-1025.

(29) Morais, R.; Vieira, D. H.; Gaspar, C.; Pereira, L.; Martins, R.; Alves, E. N. Influence of paper surface characteristics on fully inkjet printed PEDOT: PSS-based electrochemical transistors. *Semiconductor Science and Technology* 2021, 36, 125005.

(30) Torvinen, K.; Sievänen, J.; Hjelt, T.; Hellén, E. Smooth and flexible filler-nanocellulose composite structure for printed electronics applications. *Cellulose* 2012, 19, 821-829.

(31) Mariani, L. M.; Johnson, W. R.; Considine, J. M.; Turner, K. T. Printing and mechanical characterization of cellulose nanofibril materials. *Cellulose* 2019, 26, 2639-2651.

(32) Solhi, L.; Guccini, V.; Heise, K.; Solala, I.; Niinivaara, E.; Xu, W.; Mihhels, K.; Kröger, M.; Meng, Z.; Wohlert, J.; Tao, H.; Cranston, E. D.; Kontturi, E. Understanding Nanocellulose-Water Interactions: Turning a Detriment into an Asset. *Chemical Reviews* 2023, 123, 1925-2015.

(33) Reishofer, D.; Resel, R.; Sattelkow, J.; Fischer, W. J.; Niegelhell, K.; Mohan, T.; Kleinschek, K. S.; Amenitsch, H.; Plank, H.; Tammelin, T.; Kontturi, E.; Spirk, S. Humidity Response of Cellulose Thin Films. *Biomacromolecules* 2022, 23, 1148-1157.

(34) Gehlen, M. H. Kinetics of autocatalytic acid hydrolysis of cellulose with crystalline and amorphous fractions. *Cellulose* 2010, 17, 245-252.

(35) Hill, C. A.; Keating, B. A.; Jalaludin, Z.; Mahrdt, E. A rheological description of the water vapour sorption kinetics behaviour of wood invoking a model using a canonical assembly of Kelvin-Voigt elements and a possible link with sorption hysteresis. *Holzforschung* 2012, 66.

(36) Xie, Y.; Hill, C. A. S.; Jalaludin, Z.; Sun, D. The water vapour sorption behaviour of three celluloses: analysis using parallel exponential kinetics and interpretation using the Kelvin-Voigt viscoelastic model. *Cellulose* 2011, 18, 517-530.

(37) Okubayashi, S.; Griesser, U. J.; Bechtold, T. Water Accessibilities of Man-made Cellulosic Fibers—Effects of Fiber Characteristics. *Cellulose* 2005, 12, 403-410.

(38) Okubayashi, S.; Griesser, U. J.; Bechtold, T. Moisture sorption/desorption behavior of various manmade cellulosic fibers. *Journal of Applied Polymer Science* 2005, 97, 1621-1625.

(39) Deo, C.; Acharya, S. Effect of Moisture Absorption on Mechanical Properties of Chopped Natural Fiber Reinforced Epoxy Composite. *Journal of Reinforced Plastics and Composites* 2010, 29, 2513-2521.

(40) Salem, K. S.; Naithani, V.; Jameel, H.; Lucia, L.; Pal, L. A systematic examination of the dynamics of water-cellulose interactions on capillary force-induced fiber collapse. *Carbohydrate Polymers* 2022, 295, 119856.

(41) Zaccarin, A.-M.; Iii, O. Fabrication and Characterization of Soil Moisture Sensors on a Biodegradable, Cellulose-Based Substrate. *IEEE SENSORS JOURNAL* 2023.

Aspects

The following Aspects are illustrative only and do not limit the scope of the present disclosure or the appended claims. Any part or parts of any one or more Aspects can be combined with any part or parts of any one or more other Aspects.

Aspect 1. A composite, comprising: a first surface, a second surface, and a thickness between the first surface and the second surface, a porous scaffold having a plurality of pores extending from the first surface into the thickness, at least some of the plurality of pores being at least partially filled with cellulose nanofibrils, and the first surface of the composite having a root mean square (RMS) roughness of from about 0.01 to about 0.1 μm.

The RMS roughness can be, for example, from about 0.01 to about 0.1 μm, or from about 0.02 to about 0.09 μm, or from about 0.03 to about 0.07 μm, or from about 0.4 to about 0.06 μm, or even about 0.5 μm.

Aspect 2. The composite of Aspect 1, wherein the porous scaffold comprises cellulose.

Aspect 3. The composite of Aspect 2, wherein the porous scaffold is characterized as a paper. A paper can be a pulp-based paper, for example, copy paper, cardstock, or poster board.

Aspect 4. The composite of any one of Aspects 1-3, wherein the porous scaffold is biodegradable.

Aspect 5. The composite of any one of Aspects 1-4, wherein the cellulose nanofibrils extend from about 0.1 to about 100 μm into the thickness of the porous scaffold. The cellulose nanofibrils can extend from about 0.1 to about 100 μm, from about 0.5 to about 90 μm, from about 1 to about 80 μm, from about 2 to about 75 μm, from about 3 to about 70 μm, from about 4 to about 60 μm, from about 5 to about 50 μm, from about 6 to about 45 μm, from about 7 to about 40 μm, from about 8 to about 35 μm, from about 9 to about 30 μm, or from about 10 to about 20 μm into the thickness of the porous scaffold.

Aspect 6. The composite of any one of Aspects 1-4 wherein the cellulose nanofibrils extend up to about 100 μm into the thickness of the porous scaffold. For example, the cellulose nanofibrils can extent up to about 100 μm, up to about 95 μm, up to about 90 μm, up to about 85 μm, up to about 80 μm, up to about 75 μm, up to about 70 μm, up to about 65 μm, up to about 60 μm, up to about 55 μm, up to about 50 μm, up to about 45 μm, up to about 40 μm, up to about 35 μm, up to about 30 μm, up to about 25 μm, up to about 20 μm, up to about 15 μm, up to about 10 μm, up to about 5 μm, or even less than about 5 μm. It should be understood that the cellulose nanofibrils can extend only partially through the thickness of the substrate.

Aspect 7. The composite of any one of Aspects 1-6, further comprising at least one conductive feature superposed on the first surface of the porous scaffold.

Aspect 8. The composite of Aspect 7, wherein the at least one conductive feature comprises a metal.

Aspect 9. The composite of any one of Aspects 7-8, wherein the at least one conductive feature defines at least a portion of any one or more of a sensor, an interconnect, a resistor, a capacitor, an antenna, or a resonator.

Aspect 10. The composite of Aspect 9, wherein the sensor is characterized as a capacitor.

Aspect 11. The composite of any one of Aspects 9-10, wherein the sensor is configured as a humidity sensor.

Aspect 12. A sensor module, the sensor module comprising a composite according to any one of Aspects 1-11, the sensor module optionally being configured as a moisture sensor.

Aspect 13. The sensor module of Aspect 12, wherein the sensor module is configured to emit and/or receive a detectable signal, the detectable signal optionally being indicative of a state of the sensor module.

Aspect 14. A method, comprising detecting a moisture level of a medium with a sensor module according to any one of Aspects 12-13.

Aspect 15. A method, comprising: forming a composite having a first surface, a second surface, and a thickness therebetween by contacting (1) a solution of cellulose nanofibrils and (2) a porous scaffold having pores extending from a first surface of the scaffold, the contacting being performed such that at least some of the plurality of the pores are at least partially filled with cellulose nanofibrils of the solution and that the first surface of the composite has a root mean square roughness of from about 0.01 to about 0.1 μm, the solution optionally being applied through a stencil to the porous scaffold, optionally heating the solution of cellulose nanofibrils applied to the porous scaffold, and optionally compressing the porous scaffold after contacting the porous scaffold and the solution of cellulose nanofibrils. The optional compressing can optionally involve a metal fixture, and can further optionally involving a spacer sheet disposed between the porous scaffold and the metal fixture The methods can be performed by, for example, an approach as shown in FIG. 21. As shown, one can place an amount of a CNF solution atop a scaffold, for example a cardstock. Pressure can be applied with a plate, and a spacer sheet—which can comprise a rubber or other elastomer, such as polyurethane—can be placed between the CNF solution and the plate. Without being bound to any particular theory or embodiment, the presence of the spacer sheet can reduce warping of the plate as well as improve other performance. A screen—which can be an aluminum or other material screen-can be placed beneath the scaffold, and excess fluid can be expressed through the screen and then collected for disposal.

Aspect 16. The method of Aspect 15, wherein the contacting is performed such that the cellulose nanofibrils extend from about 0.1 μm to about 100 μm into the thickness of the porous scaffold.

Aspect 17. The method of any one of Aspects 15-16, wherein the porous scaffold is biodegradable.

Aspect 18. The method of Aspect 17, wherein the porous scaffold comprises cellulose.

Aspect 19. The method of any one of Aspects 15-18, further comprising forming at least one conductive feature on the first surface of the composite.

Aspect 20. The method of Aspect 19, wherein the at least one conductive feature defines at least a portion of any one or more of a sensor, a resistor, a capacitor, an interconnect, an antenna, or a resonator.

What is claimed:

1. A composite, comprising:

a first surface, a second surface, and a thickness between the first surface and the second surface, a porous scaffold having a plurality of pores extending from the first surface into the thickness, at least some of the plurality of pores being at least partially filled with cellulose nanofibrils, and the first surface of the composite having a root mean square roughness of from about 0.01 to about 0.1 μm.

2. The composite of claim 1, wherein the porous scaffold comprises cellulose.

3. The composite of claim 2, wherein the porous scaffold is characterized as a paper.

4. The composite of claim 1, wherein the porous scaffold is biodegradable.

5. The composite of claim 1, wherein the cellulose nanofibrils extend from about 0.1 to about 100 μm into the thickness of the porous scaffold.

6. The composite of claim 1, wherein the cellulose nanofibrils extend up to about 100 μm into the thickness of the porous scaffold.

7. The composite of claim 1, further comprising at least one conductive feature superposed on the first surface of the porous scaffold.

8. The composite of claim 7, wherein the at least one conductive feature comprises a metal.

9. The composite of claim 7, wherein the at least one conductive feature defines at least a portion of any one or more of a sensor, an interconnect, a resistor, a capacitor, an antenna, or a resonator.

10. The composite of claim 9, wherein the sensor is characterized as a capacitor.

11. The composite of claim 9, wherein the sensor is configured as a humidity sensor.

12. A sensor module, the sensor module comprising a composite according to claim 1, the sensor module optionally being configured as a moisture sensor.

13. The sensor module of claim 12, wherein the sensor module is configured to emit and/or a detectable signal, the detectable signal optionally being indicative of a state of the sensor module.

14. A method, comprising detecting a moisture level of a medium with a sensor module according to claim 12.

15. A method, comprising:

forming a composite having a first surface, a second surface, and a thickness therebetween by contacting (1) a solution of cellulose nanofibrils and (2) a porous scaffold having pores extending from a first surface of the scaffold, the contacting being performed such that at least some of the plurality of the pores are at least partially filled with cellulose nanofibrils of the solution and that the first surface of the composite has a root mean square roughness of from about 0.01 to about 0.1 μm, the solution optionally being applied through a stencil to the porous scaffold, optionally heating the solution of cellulose nanofibrils applied to the porous scaffold, and optionally compressing the porous scaffold after contacting the porous scaffold and the solution of cellulose nanofibrils, the optional compressing optionally involving a metal fixture, and further optionally involving a spacer sheet disposed between the porous scaffold and the metal fixture.

16. The method of claim 15, wherein the contacting is performed such that the cellulose nanofibrils extend from about 0.1 μm to about 100 μm into the thickness of the porous scaffold.

17. The method of claim 15, wherein the porous scaffold is biodegradable.

18. The method of claim 17, wherein the porous scaffold comprises cellulose.

19. The method of claim 15, further comprising forming at least one conductive feature on the first surface of the composite.

20. The method of claim 19, wherein the at least one conductive feature defines at least a portion of any one or more of a sensor, a resistor, a capacitor, an interconnect, an antenna, or a resonator.

* * * * *